(12) United States Patent
Frank et al.

(10) Patent No.: US 11,529,071 B2
(45) Date of Patent: Dec. 20, 2022

(54) METHODS FOR MANUFACTURING CAPSULES WITH INGESTIBLE EVENT MARKERS

(71) Applicant: OTSUKA PHARMACEUTICAL CO., LTD., Tokyo (JP)

(72) Inventors: Jeremy Frank, San Francisco, CA (US); Nikhil Pargaonkar, Hayward, CA (US); Raymond Schmidt, San Francisco, CA (US); Robert Azevedo, Albany, CA (US); Kurt Scheinpflug, Fremont, CA (US); Nikolaus Leist, San Carlos, CA (US); Chris Dong, San Francisco, CA (US); Hiren Patel, Redwood City, CA (US); Peter Bjeletich, Livermore, CA (US); Robert Duck, San Francisco, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/034,893

(22) Filed: Sep. 28, 2020

(65) Prior Publication Data

US 2021/0212592 A1    Jul. 15, 2021

Related U.S. Application Data

(62) Division of application No. 15/794,084, filed on Oct. 26, 2017, now Pat. No. 10,820,831.

(Continued)

(51) Int. Cl.
*A61K 9/48* (2006.01)
*A61B 5/07* (2006.01)
(Continued)

(52) U.S. Cl.
CPC ............. *A61B 5/07* (2013.01); *A61B 5/073* (2013.01); *A61J 3/07* (2013.01); *A61J 3/074* (2013.01);
(Continued)

(58) Field of Classification Search
CPC .... A61B 5/07; A61B 5/073; A61J 3/07; A61J 3/074; A61J 3/10; A61J 2200/72; A61J 3/077; A61K 9/4808; A61K 49/00
See application file for complete search history.

(56) References Cited

U.S. PATENT DOCUMENTS 1,548,459 A    8/1925    Hammer
2,587,158 A    2/1952    Hofberg
(Continued)

FOREIGN PATENT DOCUMENTS

CN    1588649    3/2005
CN    1650844    8/2005
(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.
(Continued)

*Primary Examiner* — Jermie E Cozart
(74) *Attorney, Agent, or Firm* — Pillsbury Winthrop Shaw Pittman, LLP

(57) ABSTRACT

Various methods and apparatuses are presented for an ingestible capsule that includes a digital, ingestible sensor component—or ingestible sensor—embedded into the capsule. The ingestible sensor component may be configured to activate upon coming into contact with conductive fluid, such as a body's stomach fluid. Once activated, the ingestible sensor component may be configured to perform various
(Continued)

tasks, such as transmitting one or more signals and obtaining biometric data about the body that ingested the capsule.

19 Claims, 13 Drawing Sheets

Related U.S. Application Data

(60) Provisional application No. 62/413,397, filed on Oct. 26, 2016.

(51) Int. Cl.
  *B30B 11/34* (2006.01)
  *A61K 49/00* (2006.01)
  *A61J 3/07* (2006.01)
  *B32B 37/14* (2006.01)
  *A61J 3/10* (2006.01)

(52) U.S. Cl.
  CPC ............ *A61K 9/4808* (2013.01); *A61K 49/00* (2013.01); *B30B 11/34* (2013.01); *A61J 3/10* (2013.01); *A61J 2200/30* (2013.01); *A61J 2200/70* (2013.01); *A61J 2200/72* (2013.01); *B32B 37/14* (2013.01)

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,139,589 A | 2/1979 | Beringer et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,814,181 A | 3/1989 | Jordan et al. |
| 4,844,076 A | 7/1989 | Ho |
| 4,847,090 A | 7/1989 | Della Posta et al. |
| 4,876,093 A | 10/1989 | Theeuwes et al. |
| 4,891,223 A | 1/1990 | Ambegaonakar et al. |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urquhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,187,723 A | 2/1993 | Mueller |
| 5,213,738 A | 5/1993 | Hampton et al. |
| 5,218,343 A | 6/1993 | Stobbe et al. |
| 5,261,402 A | 11/1993 | DiSabito |
| 5,263,481 A | 11/1993 | Axelgaard et al. |
| 5,273,066 A | 12/1993 | Graham et al. |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,310,301 A | 5/1994 | Aono |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,485,841 A | 1/1996 | Watkin et al. |
| 5,506,248 A | 4/1996 | Nikfar et al. |
| 5,522,512 A | 6/1996 | Archer et al. |
| 5,551,020 A | 8/1996 | Flax et al. |
| 5,567,210 A | 10/1996 | Bates et al. |
| 5,596,302 A | 1/1997 | Mastrocola et al. |
| 5,600,548 A | 2/1997 | Nguyen et al. |
| 5,603,363 A | 2/1997 | Nelson |
| 5,634,468 A | 6/1997 | Platt |
| 5,645,063 A | 7/1997 | Straka et al. |
| 5,659,247 A | 8/1997 | Clements |
| 5,703,463 A | 12/1997 | Smith |
| 5,705,189 A | 1/1998 | Lehmann et al. |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,842,324 A | 12/1998 | Grosskopf et al. |
| 5,845,265 A | 12/1998 | Woolston |
| 5,862,803 A | 1/1999 | Besson |
| 5,868,136 A | 2/1999 | Fox |
| 5,914,132 A | 6/1999 | Keim et al. |
| 5,914,701 A | 6/1999 | Gersheneld et al. |
| 5,925,030 A | 7/1999 | Gross et al. |
| 5,946,550 A | 8/1999 | Papadimitrakopoulos |
| 5,957,854 A | 9/1999 | Besson et al. |
| 5,963,132 A | 10/1999 | Yoakum et al. |
| 5,974,124 A | 10/1999 | Schlueter, Jr. et al. |

(56) References Cited

U.S. PATENT DOCUMENTS

| | | |
|---|---|---|
| 5,981,166 A | 11/1999 | Mandecki |
| 5,999,846 A | 12/1999 | Pardey et al. |
| 6,018,229 A | 1/2000 | Mitchell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |
| 6,079,284 A | 6/2000 | Yamamoto et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,205,745 B1 | 3/2001 | Dudderar et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,997 B1 | 5/2002 | Lemelson |
| 6,425,422 B1 | 7/2002 | Trebbi |
| 6,426,863 B1 | 7/2002 | Munshi |
| 6,432,292 B1 | 8/2002 | Pinto et al. |
| 6,434,911 B1 | 8/2002 | Yamamoto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,547,994 B1 | 4/2003 | Monkhouse et al. |
| 6,561,975 B1 | 5/2003 | Pool et al. |
| 6,564,079 B1 | 5/2003 | Cory |
| 6,567,685 B2 | 5/2003 | Takamori et al. |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,739,455 B2 | 5/2004 | Yamamoto et al. |
| 6,740,033 B1 | 5/2004 | Olejniczak et al. |
| 6,741,731 B1 | 5/2004 | Yamamoto et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,825,731 B2 | 11/2004 | Hasegawa |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,866,863 B2 | 3/2005 | Ribi |
| 6,879,810 B2 | 4/2005 | Bouet |
| 6,888,337 B2 | 5/2005 | Sawyers |
| 6,889,165 B2 | 5/2005 | Lind et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,942,770 B2 | 9/2005 | Cai et al. |
| 6,946,156 B2 | 9/2005 | Bunick |
| 6,951,536 B2 | 10/2005 | Yokoi |
| 6,957,107 B2 | 10/2005 | Rogers et al. |
| 6,958,603 B2 | 10/2005 | Kondo |
| 6,960,617 B2 | 11/2005 | Omidian et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,061,236 B2 | 6/2006 | Britton |
| 7,083,578 B2 | 8/2006 | Lewkowicz |
| 7,083,805 B2 | 8/2006 | Begleiter |
| 7,116,252 B2 | 10/2006 | Teraguchi |
| 7,118,531 B2 | 10/2006 | Krill |
| 7,122,143 B2 | 10/2006 | Sowden et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |

(56) References Cited

U.S. PATENT DOCUMENTS

| | | |
|---|---|---|
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,242,318 B2 | 7/2007 | Harris |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,272,433 B2 | 9/2007 | Riff et al. |
| 7,273,454 B2 | 9/2007 | Raymond et al. |
| 7,283,784 B2 | 10/2007 | Smith et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,299,034 B2 | 11/2007 | Kates |
| 7,311,665 B2 | 12/2007 | Hawthorne |
| 7,313,163 B2 | 12/2007 | Liu |
| 7,317,378 B2 | 1/2008 | Jarvis et al. |
| 7,317,621 B2 | 1/2008 | Kimura et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,443,290 B2 | 10/2008 | Takiguchi |
| 7,458,887 B2 | 12/2008 | Kurosawa |
| 7,463,918 B2 | 12/2008 | Kim et al. |
| 7,469,838 B2 | 12/2008 | Brooks et al. |
| 7,471,665 B2 | 12/2008 | Perlman |
| 7,471,992 B2 | 12/2008 | Schmidt et al. |
| 7,492,128 B2 | 2/2009 | Shen |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,584,002 B2 | 9/2009 | Burnes et al. |
| 7,598,878 B2 | 10/2009 | Goldreich |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,090 B1 | 1/2010 | Frisch et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,653,350 B2 | 1/2010 | Camp, Jr. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker |
| 7,720,036 B2 | 5/2010 | Sadri |
| 7,725,150 B2 | 5/2010 | Tupin, Jr. et al. |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,760,104 B2 | 7/2010 | Asp |
| 7,778,695 B2 | 8/2010 | Black et al. |
| 7,782,189 B2 | 8/2010 | Spoonhower et al. |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,859,401 B2 | 12/2010 | Falck et al. |
| 7,860,204 B2 | 12/2010 | Furrer et al. |
| 7,873,334 B2 | 1/2011 | Itkin et al. |
| 7,881,799 B2 | 2/2011 | Greenberg et al. |
| 7,930,064 B2 | 4/2011 | Popovich, Jr. et al. |
| 7,942,844 B2 | 5/2011 | Moberg et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,082,919 B2 | 12/2011 | Brunnberg et al. |
| 8,119,045 B2 | 2/2012 | Schmidt et al. |
| 8,131,376 B1 | 3/2012 | Faraji et al. |
| 8,134,459 B2 | 3/2012 | Smith et al. |
| 8,177,611 B2 | 5/2012 | Kang |
| 8,185,191 B1 | 5/2012 | Shapiro et al. |
| 8,185,646 B2 | 5/2012 | Headley |
| 8,200,320 B2 | 6/2012 | Kovacs |
| 8,203,991 B2 | 6/2012 | Thoukydides |
| 8,207,731 B2 | 6/2012 | Moskalenko |
| 8,224,596 B2 | 7/2012 | Agrawal et al. |
| 8,252,234 B2 | 8/2012 | Clarke et al. |
| 8,253,586 B1 | 8/2012 | Matak |
| 8,254,853 B2 | 8/2012 | Rofougaran |
| 8,271,146 B2 | 9/2012 | Heber et al. |
| 8,298,574 B2 | 10/2012 | Tsabari et al. |
| 8,323,029 B2 | 12/2012 | Toly |
| 8,343,068 B2 | 1/2013 | Najafi et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,452,366 B2 | 5/2013 | Gilland |
| 8,454,528 B2 | 6/2013 | Yuen et al. |

(56) References Cited

U.S. PATENT DOCUMENTS

| | | |
|---|---|---|
| 8,512,749 B2 | 8/2013 | Sawhney et al. |
| 8,532,776 B2 | 9/2013 | Greenberg et al. |
| 8,540,633 B2 | 9/2013 | Hafezi et al. |
| 8,540,664 B2 | 9/2013 | Robertson et al. |
| 8,545,402 B2 | 10/2013 | Hafezi et al. |
| 8,545,887 B2 | 10/2013 | Sowden et al. |
| 8,547,248 B2 | 10/2013 | Zdeblick et al. |
| 8,558,563 B2 | 10/2013 | Zdeblick |
| 8,562,526 B2 | 10/2013 | Heneghan et al. |
| 8,564,432 B2 | 10/2013 | Covannon et al. |
| 8,597,186 B2 | 12/2013 | Hafezi et al. |
| 8,597,278 B2 | 12/2013 | Trovato et al. |
| 8,634,838 B2 | 1/2014 | Hellwig et al. |
| 8,647,358 B2 | 2/2014 | Brister et al. |
| 8,660,645 B2 | 2/2014 | Stevenson et al. |
| 8,666,687 B2 | 3/2014 | Kaneko |
| 8,668,643 B2 | 3/2014 | Kinast |
| 8,672,863 B2 | 3/2014 | Lewkowicz et al. |
| 8,685,451 B2 | 4/2014 | Toneguzzo et al. |
| 8,697,057 B2 | 4/2014 | Van Epps et al. |
| 8,698,006 B2 | 4/2014 | Bealka et al. |
| 8,715,725 B2 | 5/2014 | Stuck et al. |
| 8,721,540 B2 | 5/2014 | Hafezi et al. |
| 8,744,581 B2 | 6/2014 | Mosesov |
| 8,758,237 B2 | 6/2014 | Sherman et al. |
| 8,784,308 B2 | 7/2014 | Duck et al. |
| 8,802,183 B2 | 8/2014 | Frank et al. |
| 8,816,847 B2 | 8/2014 | Zdeblick et al. |
| 8,836,513 B2 | 9/2014 | Hafezi et al. |
| 8,838,217 B2 | 9/2014 | Myr |
| 8,858,432 B2 | 10/2014 | Robertson |
| 8,881,972 B2 | 11/2014 | O'Neill et al. |
| 8,908,943 B2 | 12/2014 | Berry et al. |
| 8,912,908 B2 | 12/2014 | Berkman et al. |
| 8,926,509 B2 | 1/2015 | Magar et al. |
| 8,932,221 B2 | 1/2015 | Colliou et al. |
| 8,934,957 B2 | 1/2015 | Dias et al. |
| 8,945,005 B2 | 2/2015 | Hafezi et al. |
| 8,951,234 B2 | 2/2015 | Hafezi et al. |
| 8,956,287 B2 | 2/2015 | Zdeblick et al. |
| 8,956,288 B2 | 2/2015 | Hafezi et al. |
| 8,967,140 B2 | 3/2015 | Denyer et al. |
| 8,989,837 B2 | 3/2015 | Weinstein et al. |
| 9,011,327 B2 | 4/2015 | Schenk |
| 9,031,658 B2 | 5/2015 | Chiao et al. |
| 9,088,168 B2 | 7/2015 | Mach et al. |
| 9,107,806 B2 | 8/2015 | Hafezi et al. |
| 9,119,554 B2 | 9/2015 | Robertson et al. |
| 9,119,918 B2 | 9/2015 | Robertson et al. |
| 9,149,423 B2 | 10/2015 | Duck et al. |
| 9,158,890 B2 | 10/2015 | Meredith et al. |
| 9,161,707 B2 | 10/2015 | Hafezi et al. |
| 9,168,001 B2 | 10/2015 | Stivoric et al. |
| 9,189,941 B2 | 11/2015 | Eschelman et al. |
| 9,226,663 B2 | 1/2016 | Fei |
| 9,226,679 B2 | 1/2016 | Baida |
| 9,258,035 B2 | 2/2016 | Robertoson et al. |
| 9,268,909 B2 | 2/2016 | Jani et al. |
| 9,270,025 B2 | 2/2016 | Robertson et al. |
| 9,271,897 B2 | 3/2016 | Costello et al. |
| 9,277,864 B2 | 3/2016 | Yang et al. |
| 9,307,915 B2 | 4/2016 | McCombie et al. |
| 9,320,455 B2 | 4/2016 | Hafezi et al. |
| 9,327,076 B2 | 5/2016 | Trovato et al. |
| 9,415,010 B2 | 8/2016 | Hafezi et al. |
| 9,430,771 B2 | 8/2016 | Learmonth et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,444,503 B2 | 9/2016 | Arne et al. |
| 9,517,012 B2 | 12/2016 | Lane et al. |
| 9,597,010 B2 | 3/2017 | Thompson et al. |
| 9,597,487 B2 | 3/2017 | Robertson et al. |
| 9,599,679 B2 | 3/2017 | Taylor et al. |
| 9,649,066 B2 | 5/2017 | Zdeblick et al. |
| 9,681,842 B2 | 6/2017 | Zdeblick et al. |
| 9,741,975 B2 | 8/2017 | Laulicht et al. |
| 9,756,874 B2 | 9/2017 | Arne et al. |
| 9,796,576 B2 | 10/2017 | Thompson |
| 9,872,637 B2 | 1/2018 | Kording et al. |
| 9,883,819 B2 | 2/2018 | Jensen et al. |
| 9,900,109 B2 | 2/2018 | Bandy |
| 9,913,698 B2 | 3/2018 | Kimura et al. |
| 9,936,878 B2 | 4/2018 | Hill |
| 9,962,107 B2 | 5/2018 | Frank et al. |
| 9,968,284 B2 | 5/2018 | Vidalis et al. |
| 10,084,880 B2 | 9/2018 | Thompson et al. |
| 10,175,376 B2 | 1/2019 | Schmidt et al. |
| 10,187,121 B2 | 1/2019 | Shirvani et al. |
| 10,207,093 B2 | 2/2019 | Robertson et al. |
| 10,398,161 B2 | 9/2019 | Arne et al. |
| 10,421,658 B2 | 9/2019 | Thompson |
| 10,441,194 B2 | 10/2019 | Robertson et al. |
| 10,490,108 B2 | 11/2019 | Zhou et al. |
| 10,517,506 B2 | 12/2019 | Robertson et al. |
| 10,517,507 B2 | 12/2019 | Frank et al. |
| 10,542,909 B2 | 1/2020 | Zdeblick et al. |
| 10,588,544 B2 | 3/2020 | Hafezi et al. |
| 10,610,128 B2 | 4/2020 | Zdeblick et al. |
| 10,653,875 B2 | 5/2020 | Hafezi et al. |
| 10,758,150 B2 | 9/2020 | Saroka et al. |
| 10,797,758 B2 | 10/2020 | Shirvani et al. |
| 10,820,831 B2 * | 11/2020 | Frank ............... A61J 3/074 |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0099423 A1 | 7/2002 | Berg et al. |
| 2002/0103425 A1 | 8/2002 | Mault |
| 2002/0128934 A1 | 9/2002 | Shaer |
| 2002/0132226 A1 | 9/2002 | Nair |
| 2002/0136744 A1 | 9/2002 | McGlynn et al. |
| 2002/0161354 A1 | 10/2002 | Christiansen et al. |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0015672 A1 | 1/2003 | Gallagher |
| 2003/0017826 A1 | 1/2003 | Fishman et al. |
| 2003/0023150 A1 | 1/2003 | Yokoi et al. |
| 2003/0028226 A1 | 2/2003 | Thompson |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0091625 A1 | 5/2003 | Hariharan et al. |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |

(56) References Cited

U.S. PATENT DOCUMENTS

| | | |
|---|---|---|
| 2003/0219484 A1 | 11/2003 | Sowden et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0117062 A1 | 6/2004 | Bonney et al. |
| 2004/0121015 A1 | 6/2004 | Chidlaw et al. |
| 2004/0143182 A1 | 7/2004 | Kucera et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167465 A1 | 8/2004 | Mihai et al. |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0259899 A1 | 12/2004 | Sanghvi et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165272 A1 | 7/2005 | Okada et al. |
| 2005/0165323 A1 | 7/2005 | Montgomery |
| 2005/0172958 A1 | 8/2005 | Singer et al. |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0111777 A1 | 5/2006 | Chen |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0154642 A1 | 7/2006 | Scannell, Jr. |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0212096 A1 | 9/2006 | Stevenson |
| 2006/0216603 A1 | 9/2006 | Choi |
| 2006/0218011 A1 | 9/2006 | Walker |
| 2006/0224326 A1 | 10/2006 | St. Ores et al. |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0025739 A1 | 2/2007 | Moore et al. |
| 2007/0027386 A1 | 2/2007 | Such |
| 2007/0027388 A1 | 2/2007 | Chou |
| 2007/0029195 A1 | 2/2007 | Li et al. |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |

(56) References Cited

U.S. PATENT DOCUMENTS

| | | |
|---|---|---|
| 2007/0073353 A1 | 3/2007 | Rooney et al. |
| 2007/0078324 A1 | 4/2007 | Wijisiriwardana |
| 2007/0096765 A1 | 5/2007 | Kagan |
| 2007/0106346 A1 | 5/2007 | Bergelson |
| 2007/0114140 A1 | 5/2007 | Portier |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0000804 A1 | 1/2008 | Carey et al. |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0063703 A1 | 3/2008 | Gross et al. |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0117968 A1 | 5/2008 | Wang |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBeouf |
| 2008/0149480 A1 | 6/2008 | Bell |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0240325 A1 | 10/2008 | Agazzi et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281160 A1 | 11/2008 | Segawa |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0302695 A1 | 12/2008 | Meeren et al. |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0010321 A1 | 1/2009 | Chalopin et al. |
| 2009/0023391 A1 | 1/2009 | Falck |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076342 A1 | 3/2009 | Amurthur et al. |
| 2009/0076343 A1 | 3/2009 | James |
| 2009/0076350 A1 | 3/2009 | Bly et al. |
| 2009/0082645 A1* | 3/2009 | Hafezi ............ A61B 5/073 600/302 |
| 2009/0087483 A1 | 4/2009 | Sison |
| 2009/0088618 A1 | 4/2009 | Arneson |
| 2009/0099435 A1 | 4/2009 | Say et al. |
| 2009/0102611 A1 | 4/2009 | Quinn et al. |
| 2009/0105561 A1 | 4/2009 | Boydon et al. |
| 2009/0105567 A1 | 4/2009 | Smith et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |

(56) References Cited

U.S. PATENT DOCUMENTS

| | | |
|---|---|---|
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0019848 A1 | 1/2010 | Rossi |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0081895 A1 | 4/2010 | Zand |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0130837 A1 | 5/2010 | Matott |
| 2010/0135907 A1 | 6/2010 | Cranley et al. |
| 2010/0139672 A1 | 6/2010 | Kroll et al. |
| 2010/0143232 A1 | 6/2010 | Costello et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0191090 A1 | 7/2010 | Shin et al. |
| 2010/0199079 A1 | 8/2010 | Hibi et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagilov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2010/0322859 A1 | 12/2010 | Jones et al. |
| 2011/0009715 A1 | 1/2011 | O'Reilly et al. |
| 2011/0077660 A1 | 3/2011 | Janik et al. |
| 2011/0082356 A1 | 4/2011 | Yang et al. |
| 2011/0124983 A1 | 5/2011 | Kroll et al. |
| 2011/0134906 A1 | 6/2011 | Garudadri et al. |
| 2011/0160549 A1 | 6/2011 | Saroka et al. |
| 2011/0163871 A1 | 7/2011 | Einav et al. |
| 2011/0204483 A1 | 8/2011 | McNally et al. |
| 2011/0224912 A1 | 9/2011 | Bhavaraju et al. |
| 2011/0230732 A1 | 9/2011 | Edman et al. |
| 2011/0243483 A1 | 10/2011 | Crump et al. |
| 2011/0270135 A1 | 11/2011 | Dooley et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0032816 A1 | 2/2012 | Cho et al. |

(56) References Cited

U.S. PATENT DOCUMENTS

| | | |
|---|---|---|
| 2012/0062371 A1 | 3/2012 | Radivojevic et al. |
| 2012/0071743 A1 | 3/2012 | Todorov et al. |
| 2012/0109112 A1 | 5/2012 | Strand et al. |
| 2012/0179004 A1 | 7/2012 | Roesicke et al. |
| 2012/0245043 A1 | 9/2012 | England |
| 2012/0276451 A1 | 11/2012 | Lestriez et al. |
| 2012/0299723 A1 | 11/2012 | Hafezi et al. |
| 2013/0030366 A1 | 1/2013 | Robertson et al. |
| 2013/0129869 A1 | 5/2013 | Hafezi et al. |
| 2013/0129872 A1 | 5/2013 | Kruger |
| 2013/0131283 A1 | 5/2013 | Wang et al. |
| 2013/0144132 A1 | 6/2013 | Hafezi et al. |
| 2013/0171596 A1 | 7/2013 | French |
| 2013/0172690 A1 | 7/2013 | Arne et al. |
| 2013/0172694 A1 | 7/2013 | Zou et al. |
| 2013/0185228 A1 | 7/2013 | Dresner |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0275296 A1 | 10/2013 | Tietzen et al. |
| 2013/0328416 A1 | 12/2013 | Whitworth et al. |
| 2014/0009262 A1 | 1/2014 | Robertson et al. |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0275860 A1 | 9/2014 | Rottenberg et al. |
| 2014/0280125 A1 | 9/2014 | Bhardwaj et al. |
| 2014/0308930 A1 | 10/2014 | Tran |
| 2014/0309504 A1 | 10/2014 | Hafezi et al. |
| 2014/0349256 A1 | 11/2014 | Connor |
| 2014/0374276 A1 | 12/2014 | Guthrie et al. |
| 2015/0017486 A1 | 1/2015 | Lai |
| 2015/0080680 A1 | 3/2015 | Zdeblick et al. |
| 2015/0112243 A1 | 4/2015 | Hafezi et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0020182 A1 | 1/2017 | Schmidt et al. |
| 2017/0296799 A1 | 10/2017 | Hafezi et al. |
| 2018/0229996 A1 | 8/2018 | Thompson |
| 2019/0191006 A1 | 6/2019 | Thompson |

FOREIGN PATENT DOCUMENTS

| | | |
|---|---|---|
| CN | 101287411 | 10/2008 |
| CN | 101795202 | 8/2010 |
| DE | 10313005 | 10/2004 |
| DE | 102005007576 | 8/2006 |
| EP | 0344939 | 12/1989 |
| EP | 0526166 | 2/1993 |
| EP | 0981152 | 2/2000 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| GB | 827762 | 2/1960 |
| GB | 2419110 | 4/2006 |
| JP | 61072712 | 4/1986 |
| JP | H01285247 | 11/1989 |
| JP | 05228128 | 9/1993 |
| JP | H11195415 | 7/1999 |
| JP | 2000506410 | 5/2000 |
| JP | 2002263185 | 9/2002 |
| JP | 2002282219 | 10/2002 |
| JP | 2003050867 | 2/2003 |
| JP | 2004313242 | 11/2004 |
| JP | 2005073886 | 3/2005 |
| JP | 2005087552 | 4/2005 |
| JP | 2005102959 | 4/2005 |
| JP | 2005124708 | 5/2005 |
| JP | 2005514966 | 5/2005 |
| JP | 2005304880 | 11/2005 |
| JP | 2005343515 | 12/2005 |
| JP | 20055332328 | 12/2005 |
| JP | 2006006377 | 1/2006 |
| JP | 2006509574 | 3/2006 |
| JP | 2007200739 | 8/2007 |
| JP | 2007313340 | 12/2007 |
| JP | 2009514870 | 4/2009 |
| JP | 2009528909 | 8/2009 |
| KR | 200600977523 | 7/2006 |
| KR | 10-2011-0112378 | 10/2011 |
| TW | 200406192 | 5/2004 |
| TW | 200916136 | 4/2009 |
| TW | 201231091 | 8/2012 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001000085 | 1/2001 |
| WO | WO2001010464 | 2/2001 |
| WO | WO2001047466 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2002096347 | 12/2002 |
| WO | WO2003005877 | 1/2003 |
| WO | WO2003026630 | 4/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | WO2005105053 | 11/2005 |
| WO | WO2005110238 | 11/2005 |
| WO | WO2005123569 | 12/2005 |
| WO | WO2006001001 | 1/2006 |
| WO | WO2006021932 | 3/2006 |
| WO | WO2006027586 | 3/2006 |
| WO | WO2006028347 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006104843 | 10/2006 |
| WO | WO2006116718 | 11/2006 |
| WO | WO2006127355 | 11/2006 |

(56) References Cited

FOREIGN PATENT DOCUMENTS

| | | |
|---|---|---|
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007103835 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009106952 | 9/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010129288 | 11/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012112561 | 8/2012 |
| WO | WO2015112603 | 7/2015 |
| WO | WO2015112604 | 7/2015 |
| WO | WO2015119911 | 8/2015 |
| WO | WO2018018034 | 1/2018 |

OTHER PUBLICATIONS

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. for Gastrointestinal Endoscopy (2006) vol. 63, No. 4; 7 pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; (2003); abstract (1 page).

Barrie, Heidelberg pH capsule gastric analysis. Texbook of Natural Medicine, (1992), Pizzorno, Murray & Barrie (4 pages).

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf (14 pages).

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Description of ePatch Technology Platform for ECG and EMG, located it http://www.madebydelta.com/imported/images/DELTA_Web/documents/ME/ePatch_ECG_EMG.pdf, Dated Sep. 2, 2010; 1 page.

Dhar et al., "Electroless nickel plated contacts on porous silicon" Appl. Phys. Lett. 68 (10) pp. 1392-1393 (1996).

Eldeka., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf (5 pages).

Ferguson et al., "Dielectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. 2002, p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html (1 page).

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-lnsider (2010) http://www.e-health-insider.com/news/5910/new_'smart_pill'_monitors_medicines (1 page).

(56) References Cited

OTHER PUBLICATIONS

Hoover et al., "Rx for health: Engineers design pill that signals it has been swallowed" University of Florida News (2010) 2pp.; http://news.ufl.edu/2010/03/31/antenna-pill-2/.
International Search Report and Written Opinion for International PCT Application No. PCT/US2015/012252, dated Apr. 29, 2015.
International Preliminary Report on Patentability for International PCT Application No. PCT/US2015/012252, dated Jul. 26, 2016.
International Search Report and Written Opinion for International PCT Application No. PCT/US2017/043465, dated Nov. 8, 2017.
International Preliminary Report on Patentability for International PCT Application No. PCT/US2017/043465, dated Jan. 22, 2019.
Intromedic, MicroCam Innovative Capsule Endoscope Pamphlet. (2006) 8 pp (http://www.intromedic.com/en/product/productinfo.asp) (8 pages).
ISFET—Ion Sensitive Field-Effect Transistor; Microsens S.A. pdf document. Office Action dated Jun. 13, 2011 for U.S. Appl. No. 12/238,345; 4pp.
Jung, S. "Dissolvable 'Transient Electronics' Will be Good for Your Body and the Environment" MedGadget; Oct. 1, 2012; Online website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" (2010) http://www.medtronicdiabetes.com/products/index.html; 2 pp.
Medtronic, "Mini Med Paradigm ® Revel ™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf; 4 pp.
Melanson, "Walkers swallow RFID pills for science" Engadget (2008); http://www.engadget.com/2008/07/29/walkers-swallow-rfid-pills-for-science/ (1 page).
Minimitter Co. Inc. "Actiheart" Traditional 510(k) Summary. Sep. 27, 2005 (8 pages).
Minimitter Co. Inc. Noninvasive technology to help your studies succeed. Mini Mitter.com Mar. 31, 2009 (4 pages).
Mini Mitter Co, Inc. 510(k) Premarket Notification Mini-Logger for Diagnostic Spirometer. Sep. 21, 1999 (9 pages).
Mini Mitter Co, Inc. 510(k) Premarket Notification for VitalSense. Apr. 22, 2004 (11 pages).
Minimitter Co. Inc. VitalSense Integrated Physiological Monitoring System. Product Description. (2005) (4 pages).
Minimitter Co. Inc. VitalSense Wireless Vital Signs Monitoring. Temperatures.com Mar. 31, 2009 (3 pages).
Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Philips Respironics Products, Noninvasive Technology to Help Your Studies Succeed. 510 (k) Permanent Notification for Vital Sense. Apr. 22, 2004; http/minimitter.com/products.cfm.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/ (4 pages).
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf; pp. 1-28.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010); pp. 11-12.
"Smartlife awarded patent for knitted transducer" Innovation in Textiles News: http://www.innovationintextiles.com/articles/208.php; 2pp. (2009).
"The SmartPill Wireless Motility Capsule" SMARTPILL, The Measure of GI Health; (2010) http://www.smartpillcorp.com/index.cfm?pagepath=Products/The_SmartPill_Capsule&id=17814 (1 page).
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Target Innovations, Tablet Metal Detector, https://web.archive.org/web/20130215063351/http://www.metaldetectorindia.com/tablet-metal-detector.html, Feb. 15, 2013.
TargetPharmaceutical Metal Detector, Feb. 15, 2013 downloaded from Target Innovations, Tablet Metal Detector, Feb. 15, 2013.
Tatbul et al., "Confidence-based data management for personal area sensor networks" ACM International Conference Proceeding Series (2004) 72; 3 pages.
Tierney, M.J. et al "Electroreleasing Composite Membranes for Delivery of Insulin and other Biomacromolecules", J. Electrochem. Soc., vol. 137, No. 6, Jun. 1990, p. 2005-2006.

(56) References Cited

OTHER PUBLICATIONS

Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.

Walkey, "MOSFET Structure and Processing"; 97.398 Physical Electronics Lecture 20; 24 pages, Office Action dated Jun. 13, 2011 for U.S. Appl. No. 12/238,345.

Wang, X. et al "Resistance to Tracking and Erosion of Silicone Rubber Material under Various Types of Precipitation", Jpn. J. Appl. Phys. vol. 38 (1999) pp. 5170-5175.

Watson, et al., "Determination of the relationship between the pH and conductivity of gastric juice" Physiol Meas. 17 (1996) pp. 21-27.

Winter, J. et al. "The material properties of gelatin gels"; USA Ballistic Research Laboratories, Mar. 1975, p. 1-157.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3, 2006; pp. 6249-6252.

Youtube video Pharmaceutical Metal Detector/Tablet Metal Detector/ Capsule Metal Detector/ Dry Fruits; https://www.youtube.com/watch?v=l0126txam_s, May 12, 2012.

Zimmerman, "Personal Area Networks: Near-field intrabody communication" IBM Systems Journal (1996) 35 (3-4):609-17.

Zworykin, "A Radio Pill" Nature, (1957) 898, 179 Nature Publishing Group.

Office Action dated Oct. 29, 2021, issued in the corresponding Korean Patent Application No. 10-2019-7014882, 12 Pages.

Examination report dated Jun. 9, 2022, issued in the corresponding Australian Patent Application No. 2017348094, pp. 1-3.

\* cited by examiner

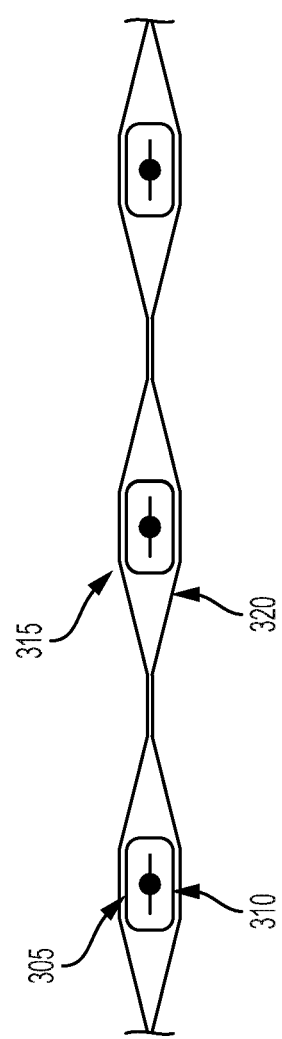

METHODS FOR MANUFACTURING CAPSULES WITH INGESTIBLE EVENT MARKERS

CROSS REFERENCE TO RELATED APPLICATION

This application is a divisional application claiming priority under 35 U.S.C. § 120 to U.S. patent application Ser. No. 15/794,084, filed Oct. 26, 2017, now U.S. Pat. No. 10,820,831, entitled METHODS FOR MANUFACTURING CAPSULES WITH INGESTIBLE EVENT MARKERS, which claims benefit under 35 U.S.C. § 119 (e) to U.S. Provisional Application No. 62/413,397, filed Oct. 26, 2016, entitled METHODS FOR MANUFACTURING CAPSULES WITH INGESTIBLE EVENT MARKERS, the entire disclosures of which are hereby incorporated by reference herein.

BACKGROUND

Digital medicine typically includes an electronic sensor component closely associated with some application of medicine, and allows for improved data tracking, such as more accurate compliance and monitoring of various physiological signals. As the medical industry transitions into the age of digital medicine, practical challenges await, such as how to efficiently and reliably incorporate digital sensors into various medicines.

SUMMARY

Various methods and apparatuses are presented for an ingestible capsule that includes a digital, ingestible sensor component—or ingestible sensor—embedded into the capsule.

In some embodiments, a method of manufacturing an ingestible capsule including an ingestible sensor is presented. The method may include: accessing an already-manufactured ingestible capsule; and modifying the capsule to include an ingestible sensor using an automated manufacturing process, wherein the ingestible sensor includes a partial power source that powers the ingestible sensor when the partial power source comes into contact with a conductive fluid.

In some embodiments of the method, modifying the capsule to include the ingestible sensor using the automated manufacturing process comprises wedging the ingestible sensor into the capsule and affixing the ingestible sensor to the capsule using friction forces between edges of the ingestible sensor and an inner wall of the ingestible capsule, using the automated manufacturing process.

In some embodiments of the method, the ingestible sensor comprises at least a portion of material that is configured to flex or deform upon applying physical pressure, and wherein wedging the ingestible sensor into the capsule comprises flexing or deforming at least a portion of the ingestible sensor as the ingestible sensor is wedged into the capsule.

In some embodiments of the method, the material that is configured to flex or deform is insoluble and non-conductive and is further configured to magnify a signal emitted from the ingestible sensor by increasing a length of a current path formed between two dissimilar materials positioned on opposite sides of the ingestible sensor.

In some embodiments of the method, modifying the capsule to include the ingestible sensor using the automated manufacturing process comprises: affixing the ingestible sensor to a first band; forming an ingestible sensor band by affixing a second band over the ingestible sensor and the first band to sandwich the ingestible sensor in between the first band and the second band; and affixing the ingestible sensor band to the capsule by wrapping the ingestible sensor band around the capsule.

In some embodiments of the method, modifying the capsule to include the ingestible sensor using the automated manufacturing process comprises: embedding the ingestible sensor onto an inner wall of an outer cap; and affixing the outer cap over at least a portion of the capsule, such that the ingestible sensor is sandwiched between at least a portion of the capsule and the outer cap.

In some embodiments of the method, modifying the capsule to include the ingestible sensor using the automated manufacturing process comprises: securing an inner wall of the capsule using a support pin; on an outer wall of the capsule, opposite the inner wall of the capsule supported by the support pin, deforming a portion of the outer wall of the capsule to create a depression, using a deforming pin; and embedding the ingestible sensor into the depression of the outer wall.

In some embodiments of the method, modifying the capsule to include the ingestible sensor using the automated manufacturing process comprises: applying a glue material to an inner wall of the capsule; and securing the ingestible sensor to the inner wall of the capsule via the glue material.

In some embodiments of the method, the glue material comprises at least one of: polyvinylpyrrolidone (PVP), hydroxypropyl cellulose (HPC), methylcellulose, ethylcellulose, gelatin or hydroxypropyl methylcellulose (HPMC).

In some embodiments of the method, modifying the capsule to include the ingestible sensor using the automated manufacturing process comprises: deforming a portion of the capsule by applying heat to the portion of the capsule; and attaching the ingestible sensor to the deformed portion of the capsule.

In some embodiments of the method, modifying the capsule to include the ingestible sensor using the automated manufacturing process comprises an ingestible sensor bead to the capsule using a fluid bed coating.

In some embodiments, another method of manufacturing an ingestible capsule including an ingestible sensor is presented. The method may include: partially forming the ingestible capsule using an automated manufacturing process; attaching the ingestible sensor to the partially formed ingestible capsule using the automated manufacturing process; and completing formation of the ingestible capsule, with the ingestible sensor included, using the automated manufacturing process, wherein the ingestible sensor includes a partial power source that powers the ingestible sensor when the partial power source comes into contact with a conductive fluid.

In some embodiments of the method, attaching the ingestible sensor to the partially formed capsule comprises wedging the ingestible sensor into a cap or partially formed body of the capsule, and affixing the ingestible sensor to the cap or partially formed body of the capsule using friction forces between edges of the ingestible sensor and an inner wall of the cap or partially formed body of the capsule.

In some embodiments of the method, the ingestible sensor comprises at least a portion of material that is configured to flex or deform upon applying physical pressure, and wherein wedging the ingestible sensor into the cap or partially formed body of the capsule comprises flexing or deforming at least a portion of the ingestible sensor as the ingestible sensor is wedged into the cap or partially formed body of the capsule.

In some embodiments of the method: partially forming the ingestible capsule comprises partially shaping capsule material using a forming pin; attaching the ingestible sensor to the partially formed capsule comprises: placing the ingestible sensor on a tip of the forming pin; and embedding the ingestible sensor into a rounded end of the partially formed capsule using the tip of the forming pin; and completing formation of the ingestible capsule comprises applying additional capsule material over the forming pin such that the ingestible sensor is attached via at least one surface of the additional capsule material that is not masked by the forming pin.

In some embodiments of the method, the ingestible sensor comprises a mating surface positioned opposite a side of the ingestible sensor adjacent to the rounded end of the capsule, the mating surface configured to mate with a drug component to be filled into the capsule.

In some embodiments of the method, the mating surface of the ingestible sensor comprises a concave shape.

In some embodiments of the method, the mating surface of the ingestible sensor comprises two straight edges connected at an acute angle.

In some embodiments of the method, attaching the ingestible sensor to the partially formed capsule comprises: coating a side of the ingestible sensor facing a distal end of the partially formed capsule with a material configured to accelerate separation of the ingestible sensor from the distal end of the capsule when the ingestible sensor is exposed to a fluid.

In some embodiments of the method, a portion of the capsule is constructed to be insoluble such that, when the capsule dissolves in a fluid, the insoluble portion of the capsule remains attached to the ingestible sensor and creates a skirt around the ingestible sensor.

In some embodiments of the method, attaching the ingestible sensor to the partially formed ingestible capsule using the automated manufacturing process comprises: casting a fast disintegrating layer of material into a distal end of the partially formed ingestible capsule; embedding the ingestible sensor onto the fast disintegrating layer of material; casting an insoluble layer of material onto the fast disintegrating layer and around the ingestible sensor; and casting a protective layer of material of material onto the insoluble layer and the ingestible sensor.

In some embodiments of the method, attaching the ingestible sensor to the partially formed capsule comprises: placing the ingestible sensor in a distal portion of the partially formed capsule; and completing formation of the ingestible capsule comprises crimping the partially formed capsule around the ingestible sensor such that the ingestible sensor is securely fastened within the distal portion of the capsule.

BRIEF DESCRIPTION OF DRAWINGS

Some embodiments are illustrated by way of example and not limitation in the figures of the accompanying drawings.

FIG. 3 shows a diagram of how the IEM may be included into a banding ribbon.

DETAILED DESCRIPTION

Figure 1:
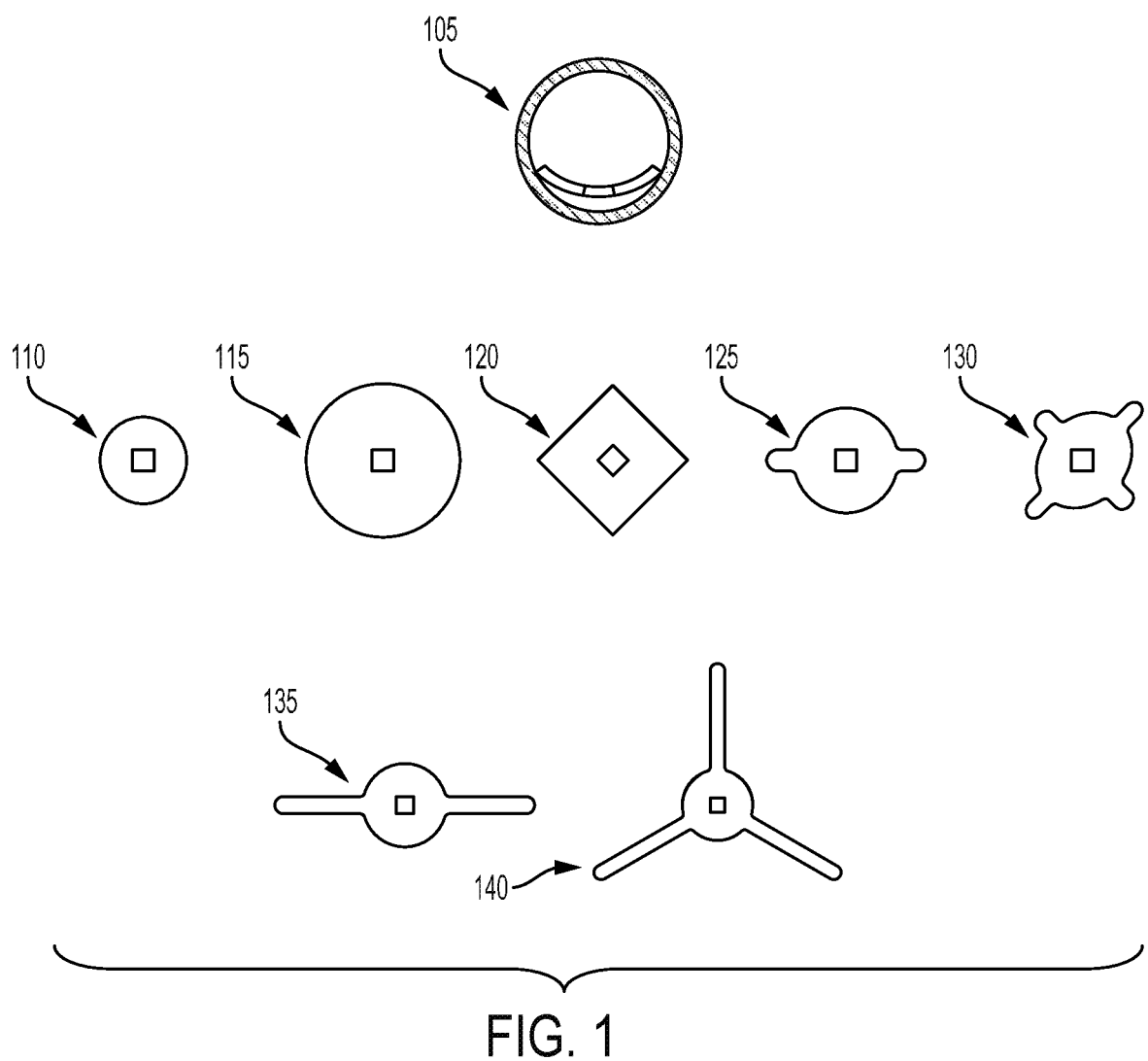
FIG. 1 illustrates various example geometries of a friction fit ingestible sensor package into a capsule.

In the following description, reference is made to the accompanying drawings that illustrate several embodiments of the present invention. It is understood that other embodiments may be utilized and mechanical, compositional, structural, and electrical operational changes may be made without departing from the spirit and scope of the present disclosure. The following detailed description is not to be taken in a limiting sense, and the scope of the embodiments of the present invention is defined only by the claims of the issued patent.

Various methods and apparatuses are presented for an ingestible capsule that includes a digital, ingestible sensor component—or ingestible sensor—embedded into the capsule. The ingestible sensor component may be configured to activate upon coming into contact with conductive fluid, such as a body's stomach fluid. Once activated, the ingestible sensor component may be configured to perform various tasks, such as transmitting one or more signals and obtaining biometric data about the body that ingested the capsule. Examples of an ingestible sensor component are an ingestible event marker (IEM) or a Mini-IEM Tablet (MIT). The ingestible sensor may also be referred to herein as a sensor pill (SP), IEM, and/or ingestible sensor microchip. The ingestible sensor includes a partial power source that is fully activated upon contact with a conductive fluid, and a circuit coupled to the partial power source and configured to perform one or more functions to transmit data through the body that ingested the capsule. As used herein, the process of including an ingestible sensor component into a capsule may be referred to as "digitizing" the capsule.

To improve mass production and manufacturing efficiency, it is desirable to create a stand-alone "digital" capsule that can then be used on standard pharmaceutical capsule-filling equipment to digitize any drug. Just placing an IEM in a capsule at the time of drug fill requires a custom piece of high-volume manufacturing equipment at every contract manufacturing organization (CMO) or partner that manufactures an encapsulated digital medicine. That approach can be expensive and may limit the number of CMOs that would be interested in manufacturing encapsulated digital medicines.

Simplistic methods for digitizing a capsule may create problems. For example, placing an ingestible sensor "loose" in a capsule may allow it to move around in an uncontrolled way that could impact device performance. In addition, loose ingestible sensors may also fall out of capsules during the encapsulation process causing product-quality concerns. The various embodiments of the present disclosures fix the ingestible sensor in a known and controlled location. Described below are a number of embodiments that may address how to digitize an ingestible capsule, particularly in accordance with known manufacturing techniques for creating ingestible capsules in general.

As described, some of the example methods provide manufacturing processes for including the ingestible sensor with a capsule after the capsule has already been manufactured, i.e., post-capsule manufacturing. These methods may be used to modify existing capsules using an additional automated manufacturing process that utilizes existing capsule manufacturing processes. Also described are some example methods for utilizing a single manufacturing process that includes the ingestible sensor with a capsule during the capsule manufacturing.

Friction Fit Ingestible Sensors

In some embodiments, an ingestible sensor is inserted in a capsule in such a way that it is held in place by deforming some portion of the ingestible sensor and/or the capsule cap or body itself. This "friction fit" is sufficient to keep the ingestible sensor in the capsule during all the downstream shipping and manufacturing steps to make a digital medicine.

The geometry of the ingestible-sensor skirt can be modified to create features that flex or deform as part of the insertion process used to place the ingestible sensor in the capsule. Those features could include adding "corners," "feelers," or simply making the ingestible-sensor skirt larger than the inner dimension of the capsule cap or body. In general, the skirt around the ingestible sensor is made of insoluble, non-conductive material that effectively amplifies the signal being transmitted from the ingestible sensor. The ingestible sensor typically creates a signal by modulating a current formed by the conductive fluid connecting two dissimilar materials located on opposite sides of the ingestible sensor. The length of the current path is increased using the skirt material, thereby increasing the strength of the signal formed by the current path. Here, the skirt material may also be used to provide friction to securely wedge the ingestible sensor into the capsule. The same insoluble, non-conductive material may also be flexible or deformable to a degree to allow bending that increases the forces of friction. FIG. 1 illustrates various example geometries of a friction fit ingestible sensor package into a capsule. Diagram 105 shows an example of a cross-sectional area of a capsule with an ingestible sensor wedged into one side of the capsule. As shown, the ingestible sensor in this case is bent or deformed partially, to fit into a side of the capsule. This "friction fit" may help maintain an ingestible sensor to stably stay in the capsule, and prevent loss during supply chain or manufacturing activities.

Ingestible sensors 110, 115, 120, 125, 130, 135, and 140 show additional examples of geometries that may be used to provide a "friction fit" into the capsules. The center module shown in each of the examples shows where the ingestible sensor may be placed, while the material around the ingestible sensor represents a skirt material that is insoluble and may be used to enhance the signal transmission capabilities when the ingestible sensor is activated. Ingestible sensor 110 shows a standard size sensor. Ingestible sensor 115 shows an "oversized" sensor with a large skirt. Ingestible sensor 120 shows a rhombus shaped skirt. Ingestible sensor 125 shows a double-lobed skirt, while ingestible sensor 130 shows four lobes around the skirt. Ingestible sensor 135 shows two long arms of the skirt in a "feeler" configuration, that may be used to deter the ingestible sensor from getting wedged to a side wall of the stomach or other area where conductive fluid is needed to reach opposite sides of the ingestible sensor. The sensor 140 includes a triple arm configuration for the skirt, to further enhance these capabilities. The "friction fit" method may be used both during a manufacturing process that integrates the ingestible sensor pill or tablet into the capsule during the capsule manufacturing process, and post-process of capsule manufacturing, i.e., modifying an existing capsule to include the ingestible sensor.

Though aspects of the present disclosure are applicable to ingestible sensors placed in the capsule body or cap, placing the ingestible sensor in the cap of a capsule may reduce the risk of the ingestible sensor interfering with the drug blend or tablet that is placed in the body of the capsule during the encapsulation process. The capsule material may act as a barrier between the drug blend/pellets and the IEM.

Ingestible Sensor Capsule Band

Figure 2:
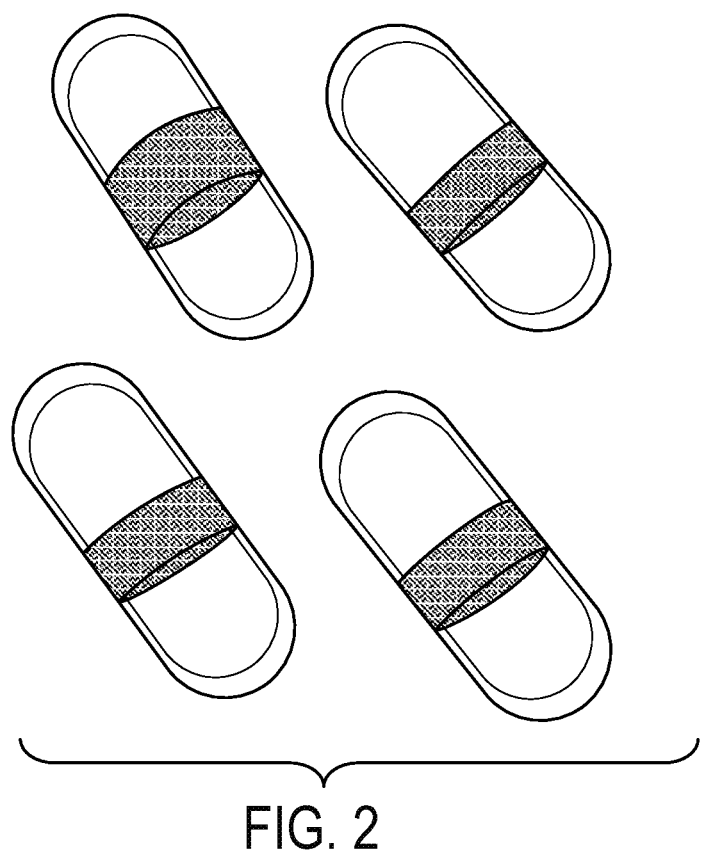
FIG. 2 shows an illustration of capsules having a band around them.

In some embodiments, an ingestible sensor may be placed within a band that encapsulates the body of a capsule. FIG. 2 shows an illustration of capsules having a band around them. The ingestible sensor may be manufactured to fit within the band. Example processes for creating a band are known, such as the Quali-seal process originally developed by Shionogi, Capsugel processes, or R.P. Scherer Hardcapsule processes. The bands being included around a capsule may be an example of adding the ingestible sensor post-capsule manufacturing. Further, this may be an example where no mechanical change to the capsule itself is required. This may allow for certain capsules to be more easily retrofitted to include ingestible sensors, and/or allow for certain capsule manufacturing processes to easily integrate ingestible sensors.

FIG. 3 provides an example for how to include the ingestible sensor into the band, a band ribbon of IEMs is created using standard film lamination techniques. The IEM 305 is sandwiched in between the band layers 315 and 320. Additionally, materials, such as loose or compacted materials 310, may be added around the IEM 305 to enhance IEM detachment upon contact with fluids. The band may be compatible with existing banding equipment. A standard roll-to-roll web-processing manufacturing tool can be used to create the banding ribbon. This process is typically performed by an automated machine that can precisely and quickly assemble these components. This process may allow for the adding of the ingestible sensor post-capsule manufacturing.

In this way, existing techniques for developing and filling capsules may not need to be modified in order to incorporate an ingestible sensor. This process may then be applied to any capsule that the band may fit around, increasing the universality of inclusion of the ingestible sensor.

Molded Sensor-to-Capsule Attach Method

In some embodiments, an IEM or Sensor Pill (SP) (e.g., IEM in placebo tablet) is molded into a capsule in such a way that it is held in place via drying or curing of the capsule material in direct contact with the sensor device during the capsule forming process. This method of attachment is sufficient to keep the IEM/SP in the capsule during all the downstream shipping and manufacturing steps to make a digital medicine and to maintain a unique orientation relative to the capsule and the subsequent drug load. The construction materials for the sensor pill can be chosen to not only optimize the coating process and adhesion between sensor pill and capsule, but also to optimize the sensor performance based on capsule material of construction (e.g., gelatin, hydroxypropyl methylcellusose, or carrageenan).

For example, choice of binders or disintegrants may assist with separation of capsule and sensor in the stomach.

Figure 4A:
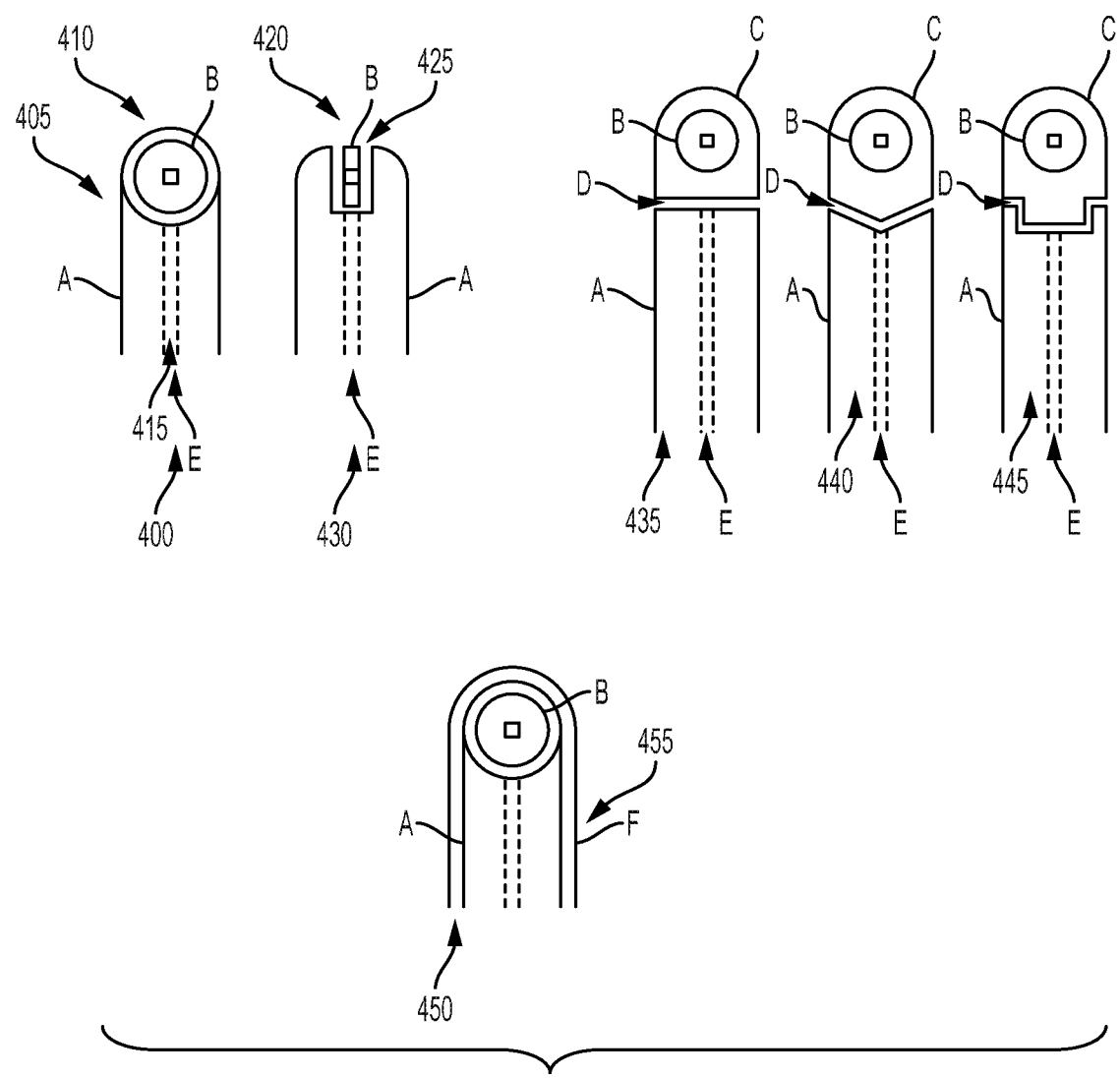
FIGS. 4A-4B illustrate a number of variations for how an ingestible sensor may be molded into a capsule.
Figure 4B:
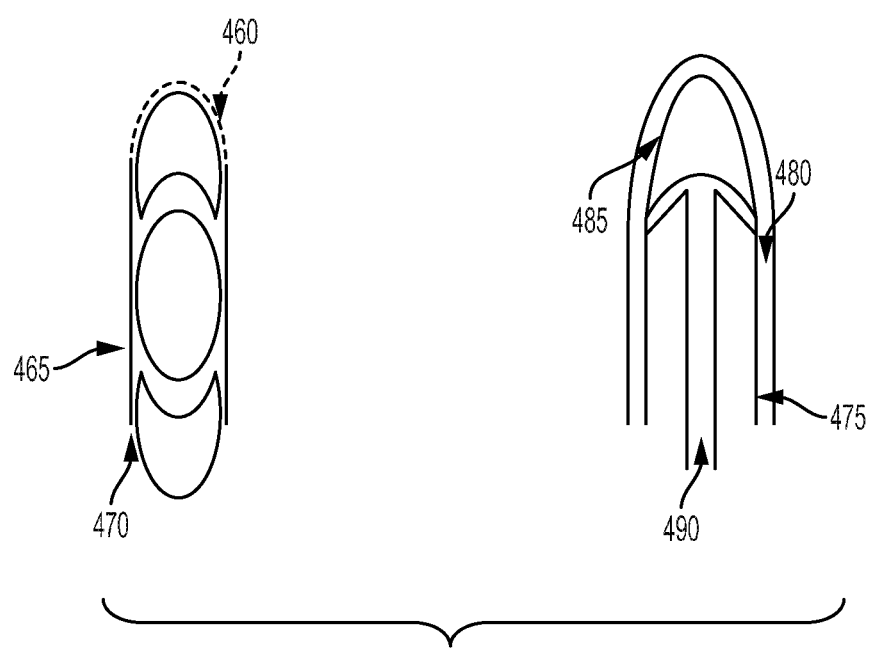

FIGS. 4A and 4B illustrate a number of variations for how an ingestible sensor may be molded into the capsule. As an example process consistent with FIG. 4A for molding the IEM into the capsule, illustration 400 shows a front view of a process for forming the capsule with an IEM using a forming pin 405, while illustration 430 shows a side view of the same. The capsule forming pin 405 would have a vertical channel machined into the rounded tip 410 in a shape to accommodate the IEM 420 held vertically. Prior to applying the capsule material to the forming pin 405, an IEM 420 is placed into the vertical channel 425 such that the circumference of the IEM 420 is approximately flush with the radius of the rounded tip 410. A small vacuum port 415 may be included within the forming pin 405 to help keep the IEM 420 in place. Capsule material 455 is then applied over the pin holding the IEM such that the outer surface is smooth and the IEM is intimately attached around the portion of its edge that was exposed (see illustration 450).

As an example process consistent with FIGS. 4A and 4B for molding the sensor pill into the capsule, the rounded tip of the forming pin is replaced with a tip geometry that mates with one surface of the sensor pill. The mating surface of the sensor pill can be flat (see illustration 435), shaped to enhance capsule forming process (see illustrations 440 and 445), or concave to allow for greater tablet volume of the finished digital capsule. The non-mating surface(s) of the sensor pill can be shaped to mimic the rounded end of a standard capsule (useful for taking advantage of standard capsule filling equipment), have custom geometry to differentiate the capsule as having a digital element, or have more pronounced taper for enhanced swallowability. Capsule material is then applied over the pin holding the sensor pill such that the outer surface is smooth and the sensor pill is intimately attached via the surface(s) that were not masked by the forming pin.

FIG. 4B shows an example of an assembled digital capsule with the sensor pill 460 attached to one end of the drug tablet 465. In this example, the mating surface connecting to the drug tablet is shaped in a concave manner. The sensor pill 460 and drug tablet 465 combination may then be coated to encase the entire combination. In this example, a second sensor pill 470 is connected to the opposite end of the drug tablet 465 for increased power and functionality. To form the tapered capsule, as shown, a forming pin 475 may be used to press the sensor pill 485 into a defined shape, in combination with a vacuum port 490. The drug tablet may then be pressed against the sensor pill at the mating surface. The capsule material 480 covers the combination of the different components.

If the forming pin must be dipped into solution of capsule material, the IEM or sensor pill can be held in the forming pin via the application of very slight vacuum. Alternatively, the capsule can be formed via spray coating capsule material onto forming pin with IEM or sensor pill in upright position (see FIGS. 4A and 4B).

The described techniques for forming capsules to sensor are applicable to both the cap and body portion of the capsule.

In this way, the molded process may allow for a single step manufacturing process (i.e., no secondary process to attach sensor after capsule is formed). In addition, the formulation of the molded process fixes orientation of the sensor within the capsule for predictable sensor performance, fixes orientation of the sensor within capsule body for consistent filling of drug contents (i.e., movement of sensor is impeded to eliminate potential air pockets that could not fill with drug), and fixes sensor to capsule such that it is not dislodged/removed during drug filling of the capsule.

Double Capsule with Ingestible Sensor

In some embodiments, the ingestible sensor may be included into a capsule by designing the empty capsules with two caps, of which one (inner) will fit inside the second (outer) cap to form a snug fit and leaving enough space for the IEM or sensor pill to be placed between the caps. The top portion of the inner cap may be shaped slightly flat to accommodate the IEM or sensor pill placement.

Figure 5:
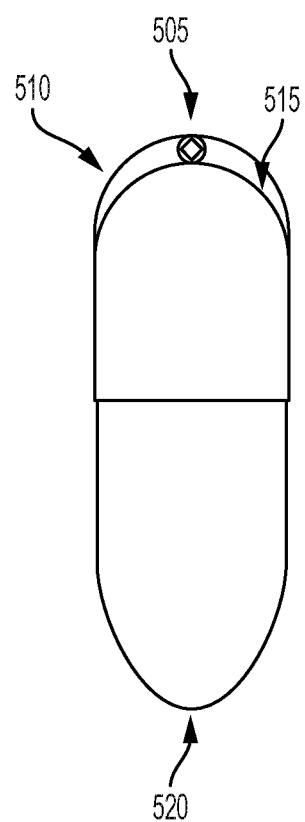
FIG. 5 provides an example of a double cap capsule that includes the ingestible sensor.

FIG. 5 provides an example of a double cap capsule that includes the ingestible sensor. The IEM or sensor pill 505 may be placed inside the outer cap 510 first, then the inner cap 515 may be fit snugly into the outer cap, securing the IEM or Sensor Pill 505. The capsule filling and formulation process may then proceed as normal in accordance with desired manufacturing techniques, until the rest of the body 520 of the capsule is formed. Placing the ingestible sensor in between the two caps of a capsule reduces the risk of the ingestible sensor interfering with the drug blend or tablet that is placed in the body of the capsule. This is another example of including the IEM or sensor pill to the capsule post-capsule manufacturing, and without requiring a mechanical modification to the existing capsule.

Sensor-to-Capsule Wall Attach Methods

In some embodiments, an IEM or sensor pill is lodged into the wall of a capsule via one of the following methods:
Casting or molding during capsule forming;
Pressure and/or temperature attachment;
Press fit into hole punched in capsule; and
Adhesive fixed into hole punched in capsule.

Figure 6:
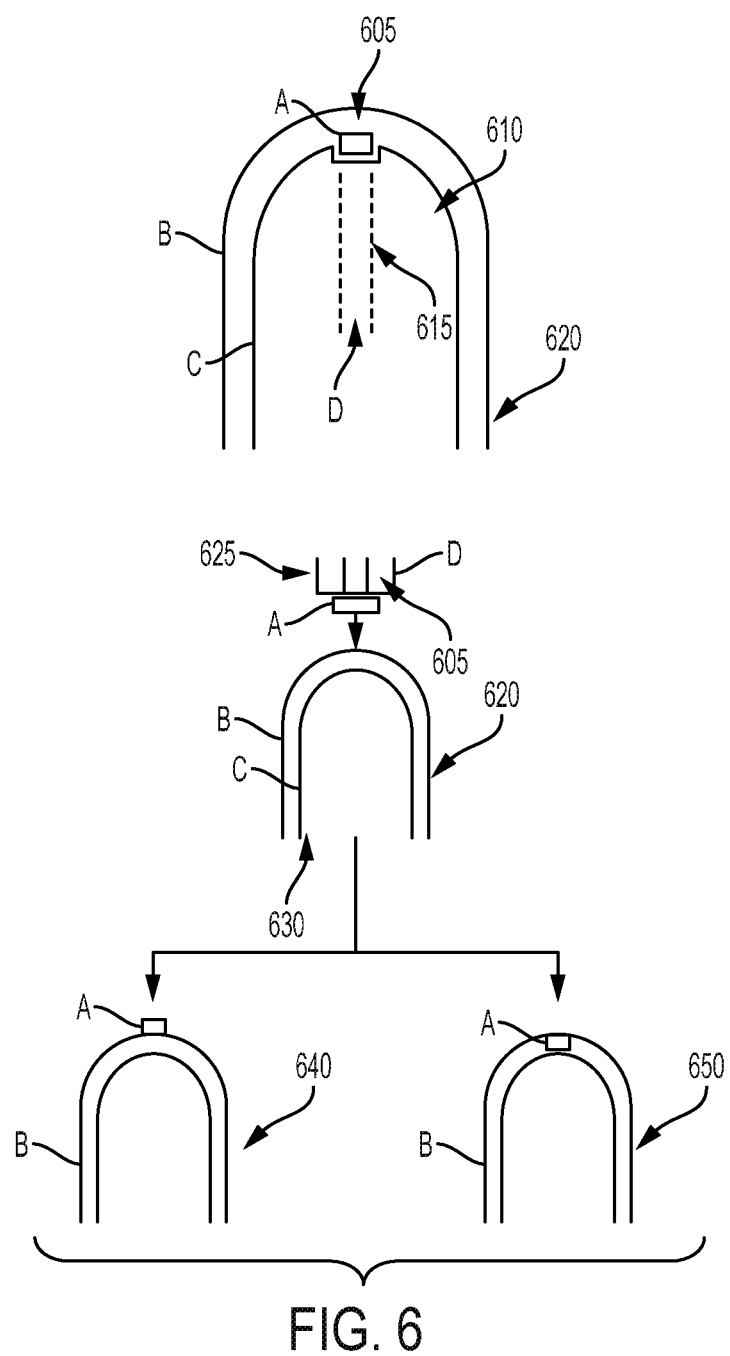
FIG. 6 provides various illustrations of the different formulations for including the IEM or other ingestible sensor into a capsule wall.

FIG. 6 provides various illustrations of the different formulations for including the IEM 605 or other ingestible sensor into a capsule wall. The portion of the capsule wall into which the IEM circuit is fixed may include standard capsule materials 620 or materials for enhanced function of the IEM circuit (e.g., material composition similar to the existing IEM skirt for signal strength enhancement).

In embodiments in which one electrode face of the IEM integrated circuit is in contact with the capsule wall, a coating can be applied to the IEM electrode face prior to attaching to the capsule to aid in affixing the IEM circuit to the wall and/or accelerate the separation of IEM circuit and capsule material when exposed to aqueous/acidic conditions like those present in the stomach.

In some embodiments, for casting/molding during capsule forming, a depression with shape similar to IEM circuit may be placed on an end of a forming pin 610. The IEM circuit 605 may be placed in a depression via vacuum pick-and-place. Positioning/hold of the circuit may be assisted via a vacuum port 615 on the forming pin 610. Capsule material is then formed on the pin via dip coating, spray coating, or other deposition techniques. A capsule with the IEM circuit is then removed from the forming pin. Multiple IEM circuits may be placed in both the body and cap portion of capsule for redundant signal transmission.

In some embodiments, for pressure/temperature attach methods, the IEM circuit 605 may be pressed against the wall of capsule via pick-and-place tip 625 capable of applying enough heat or pressure to affix the circuit to the wall. The pick-and-place tip 625 may be pressure based or temperature based. During application of heat and/or pressure, the capsule wall 620 may deform and thin next to the circuit electrode surface being pressed against the capsule. A support pin 630 may provide definition to the capsule wall 620 as the IEM 605 is being pressed into the capsule wall 620. Heat may be applied via conduction from the place tip 625 or via a non-contacting method (e.g. convective, radiative heating). Illustration 640 shows an example of the placement of the IEM onto the capsule with low temperature or pressure applied, while illustration 650 shows an example of the placement of the IEM onto the capsule with high temperature or pressure applied.

In some embodiments, for press fit attach methods, a hole with slightly smaller dimensions than the IEM integrated circuit is punched into any surface of capsule. The IEM circuit is then placed into the hole via pick-and-place tip that applies enough pressure to push the circuit to sit flush in the capsule wall.

In some embodiments, for adhesive attach methods, a hole is punched into any surface of the capsule. The hole size can range from slightly undersized (creating friction fit to assist in hold) to slightly oversized (allowing for separation between circuit and wall or space for adhesive to fill in for better hold). The IEM circuit is then placed in the hole via pick-and-place manufacturing operations. Adhesive is then applied either around edges of circuit or as a drop covering entire surface of circuit. Adhesives used may be set via drying, curing, cross-linking, or other means of action.

In some embodiments, a portion of the capsule wall that connects to the ingestible sensor may be constructed to be insoluble. This portion may be shaped in a way so as to add wings or a skirt around the ingestible sensor. Thus, when the capsule wall dissolves, the insoluble skirt and ingestible sensor will remain, and the skirt may amplify the reach of the ingestible sensor signal when activated.

Pick-and-place tips for circuit handling may be based on vacuum hold or mechanical grip and may include functionality to simultaneously place circuit and apply heat, pressure, or adhesive.

By employing any of these example methods for placing the ingestible sensor into the capsule wall, the orientation of the sensor on capsule wall may be fixed to create predictable sensor performance. In addition, there may be less occlusion of internal capsule volume allowing for maximum volume of drug product to be filled in a given capsule size. Also, these methods may fix the sensor to the capsule such that it is not dislodged/removed during drug filling of the capsule. These examples associated with FIG. 6 are other examples of integrating the IEM or sensor pill into the capsule during the capsule manufacturing process. Alternatively, embedding the IEM or sensor pill in the ways described associated with FIG. 6 may occur post-capsule manufacturing. For example, an additional process of creating a hole through a portion of an existing capsule to embed the IEM or sensor pill may occur.

Digital Capsule with Glued or Mold Casted Sensor

Since gelatin or hydroxypropylmethylcellulose are the most common materials used for capsules, choices are limited, so there is a need to tailor the ingestible sensor such that it would function well in these types of capsules. The glue or casting material is one which would hold the die (ingestible sensor microchip), IEM, or sensor pill in place within the capsule shell. The glue or casting material composition could be, but is not limited to, polyvinylpyrrolidone (PVP), hydroxypropyl cellulose (HPC), methylcellulose, ethylcellulose, gelatin or hydroxypropyl methylcellulose (HPMC).

In some embodiments, a die, IEM, or sensor pill is attached to a location inside a capsule shell held by a glue or casting material. This digitized capsule then allows for downstream shipping and manufacturing steps to make a digital medicine capsule product.

FIGS. 7A-7D illustrate various embodiments for how the ingestible sensor may be attached to the capsule 715 via glue or casting material 705. In case of glue or casting material 705, it hardens, cures or dries such that it holds the die (ingestible sensor microchip) 710, ingestible sensor, or sensor pill in place. In the case of the casting material, it could act as a skirt to enhance the sensor performance.

Figure 7A:
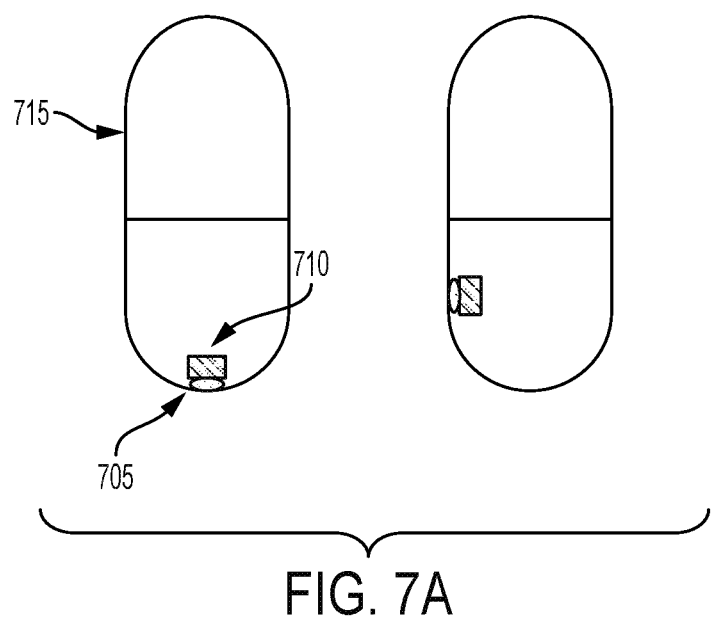
FIGS. 7A-7D provide examples of a digitized capsule using molded or casted methods.
Figure 7B:
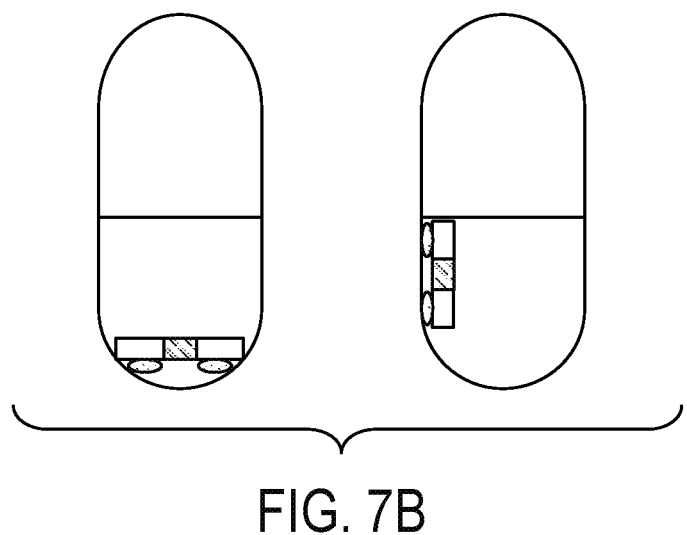
Figure 7C:
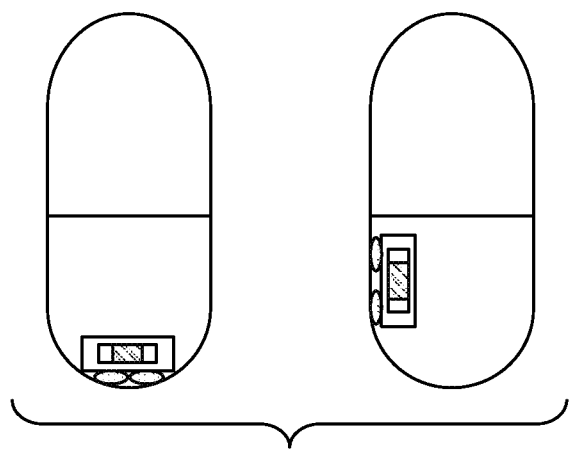

In some cases, the glue material 705 holds the die (ingestible sensor microchip) 710, IEM, or sensor pill in place within the capsule 715. This could be at the bottom of the capsule shell on either end, or on the side walls, as shown in the various examples. The conceptualized picture of the three various digitized capsules are shown in FIGS. 7A-7C.

Alternatively, the die could be placed on the bottom of the capsule, upon which a cast material is then filled. The cast material not only functions to hold the die in place, but also functions as a skirt to improve the sensor performance.

The type of glue or casting material could be various hydrogel or other polymeric materials specially formulated to meet desired properties.

The amount of glue or casting material could be varied as part of a manufacturing process that drops a fixed amount into the capsule half shell. Multiple drops of glue could be employed to fix the die, IEM, or sensor pill in place.

Figure 7D:
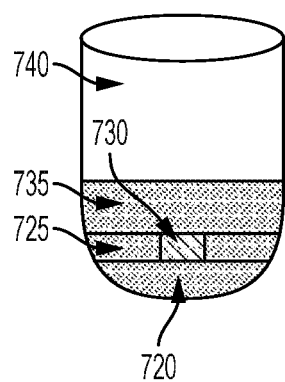

For the casting method, as shown in FIG. 7D as an example, there could be multiple layers casted in a manufacturing process involving different cast materials with the die sandwiched in between. Shown in FIG. 7D is half of a capsule shell 740 with layers at a distal end that include the die 730. Each layer could have a unique function, such as a fast dissolving or disintegrating bottom layer 720, followed by the second skirt layer 725 with the die (IEM or other ingestible sensor) 730 embedded in it, then finally a top layer 735 that protects the sensor (see FIG. 7D). This may be another example of including the IEM or sensor pill to the capsule post-capsule manufacturing, and without requiring a mechanical modification to the existing capsule. Alternatively, the example processes as described and associated with FIGS. 7A-7D may be included during a capsule manufacturing process. For example, the ingestible sensor may be placed inside the capsule and glued or otherwise attached before the drug component is filled into the capsule.

Various Mechanical or Thermo-Mechanical Methods for Attaching Ingestible Sensors to Capsules In some cases, use of forming either mechanically or thermo-mechanical and optionally using adhesives or the thermo-mechanical process to bond the ingestible sensor to the capsule creates a method of integration and securing the ingestible sensor in the capsule.

In some embodiments, an ingestible sensor is inserted in a capsule in such a way with the addition of mechanical or thermo-mechanical methods that can deform parts of the IEM skirt to ensure fit into the capsule. Further, the thermal process can be used attach the ingestible sensor to the capsule.

As an example process for implementing this, an ingestible sensor is inserted in a capsule in such a way with the addition of mechanical or thermo-mechanical methods that can deform parts of the ingestible sensor skirt to ensure fit into the capsule.

Figure 8:
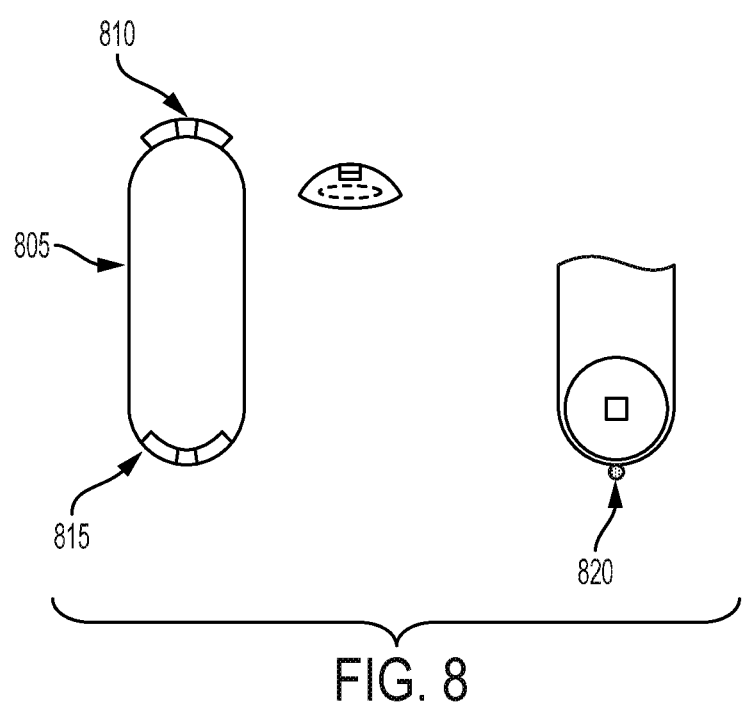
FIG. 8 shows an example illustration for a capsule that includes an ingestible sensor via thermo-mechanical techniques.

Further, the thermal process can be used to attach the ingestible sensor to the capsule. This can be done either on the external or internal surfaces of the drug capsule. This can be implemented either in the end (forming a cone) or along the sides of the capsule (forming an arch). FIG. 8 shows an example illustration for a capsule that includes an ingestible sensor in this way. The capsule 805 shows examples of an IEM 810 formed outside of the capsule, and also and an IEM 815 formed on the inside of the capsule. Notice the curved structure of the skirt portions of the IEMs. In some embodiments, a drop of glue or other adhesive 820 may also be added to aide the process.

Forming could be done against the capsule body, most likely with a forming pin or other support inside the capsule during forming. The forming head would apply heat to the IEM and generally would have the desired matching shape as the location of attachment on the capsule.

Alternately, the capsule attach can be done using an adhesive, such as a small edible glue dot as shown in the lower figures. Glue could be applied either to attach the IEM flat or perpendicular to the surface of the capsule. The latter could be preferred to secure the IEM without adding glue over the electrochemical layers on the circuit.

By employing one of these methods, integration of the ingestible sensor to the capsule is achieved in a method that does not require a priori shaping of the IEM for different capsule types/sizes because the forming can happen at the time of attachment. Also, the glue attach method perpendicular to the capsule edge could secure but also ensure the electrochemical materials are stood clear of the gelatin material to ensure activation. This may be another example of including the IEM or sensor pill to the capsule post-capsule manufacturing, and without requiring a mechanical modification to the existing capsule. Alternatively, the example processes as described and associated with FIGS. 7A-7D may be included during a capsule manufacturing process. For example, the ingestible sensor may be placed inside the capsule and formed onto the capsule wall before the drug component is filled into the capsule.

Ingestible Sensor Beads

In some embodiments, a solution to digitize any existing capsule size, finished encapsulated dose form, may be created by adding an IEM bead to the capsule. A technique called fluid bed coating may be applied to create IEM beads. Fluid bed (FB) coating can coat several functional/nonfunctional material layers over a substrate. The technique is commonly used in pharmaceutical industry to coat excipient substrates (beads).

Figure 9C:
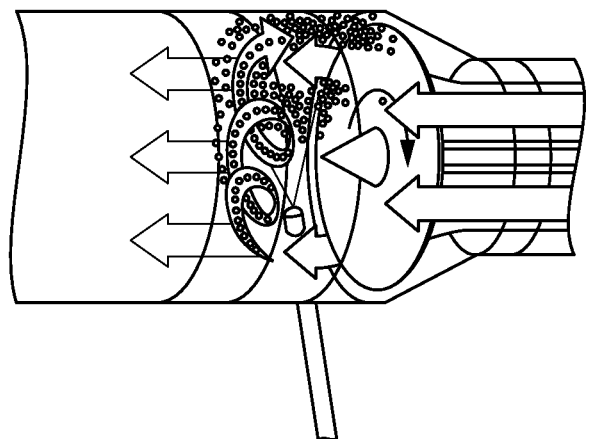
FIGS. 9A-9C show various examples of spray techniques for an ingestible sensor as a microbead in a capsule.
Figure 9B:
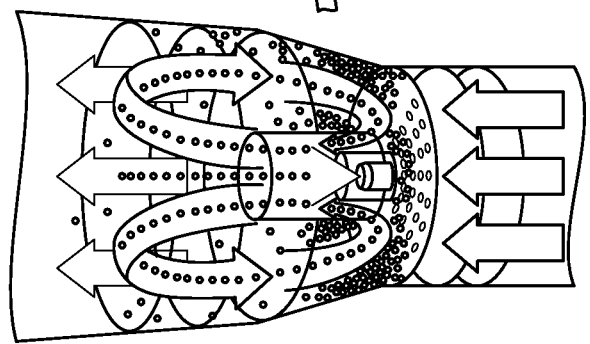
Figure 9A:
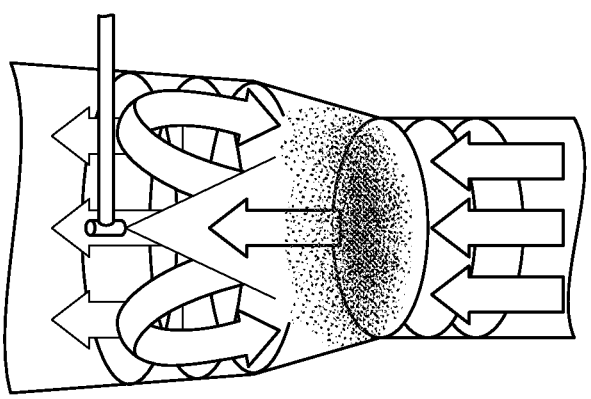

Three variants of spray techniques can be used: Top spray (FIG. 9A); Bottom spray (Wurster Column) (FIG. 9B); and Side spray (FIG. 9C).

Figure 10:
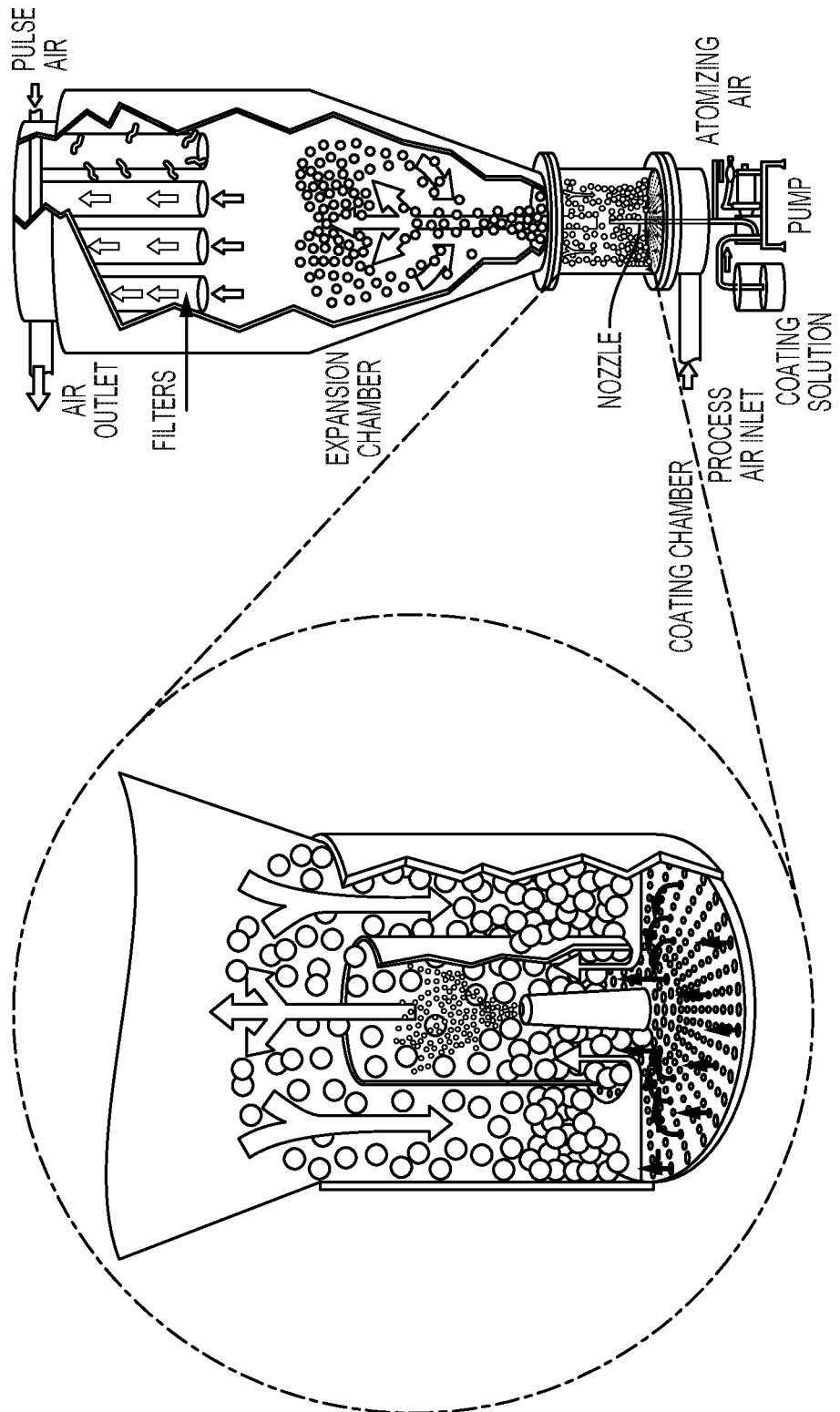
FIG. 10 shows a fluid bed system for the microbead concept.

IEMs (bare without Ethyl Cellulose skirt) or other ingestible sensor microchips can act as a base substrate that can be coated in a fluid bed coater with functional/nonfunctional coating materials to impart specific properties on to the IEM. FIG. 10 of a FB system demonstrates this concept. The coated IEMs (IEM Beads) can then be dropped into a capsule in addition to its drug payload. The IEM bead would be designed to activate soon after it interacts with the gastric fluids, whereas the drug (granules, pellets etc.) can act independent of the IEM as per its intended design.

As one example for employing this method, the base die (ingestible sensor microchip without skirt material) can be obtained from a subset of the current manufacturing process. The base die can then be used in a FB coating system to impart functional/nonfunctional coatings. The coated beads then can be added to multitude of capsule dose forms to establish the proof of concept. This may be another example of including the IEM to the capsule post-capsule manufacturing, and without requiring a mechanical modification to the existing capsule.

Additional Attachment Methods

Figure 11A:
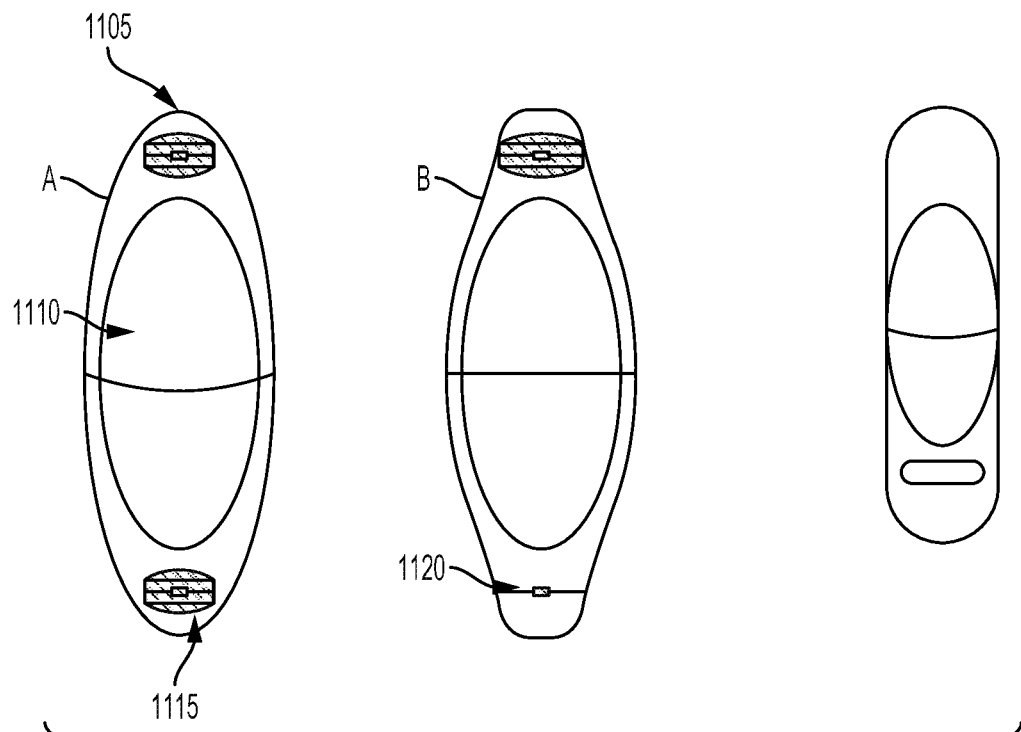
FIGS. 11A-11B provide additional examples of how a sensor pill or tablet can be placed with a drug tablet or other blend during the manufacturing process of the capsule, according to some embodiments.
Figure 11B:
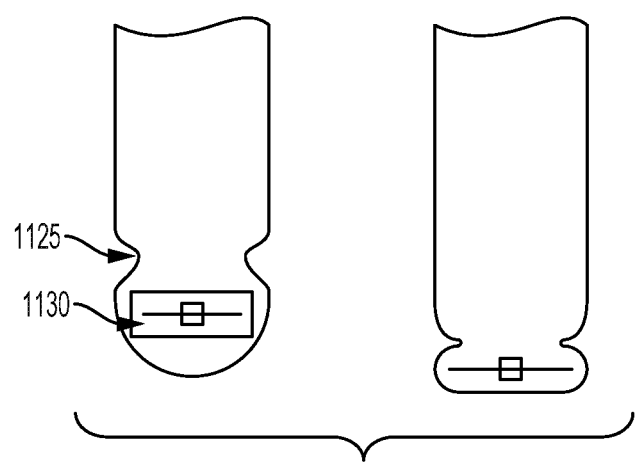

FIGS. 11A and 11B provide additional examples of how a sensor pill or tablet can be placed with a drug tablet or other blend during the manufacturing process of the capsule, according to some embodiments. In FIG. 11A, the drug tablet 1110 is shown in the middle of the capsule material, while two sensor pills or tablets 1105 and 1115 are positioned at the far ends. Tablets 1105 and 1115 are shown, while the IEM 1120 is shown as an alternative example of an ingestible sensor located at a far end of the capsule. The capsule may be manufactured in two pieces first, such as the top half and the bottom half. The sensor pill or tablet may be pre-populated into the far end of the capsule material during the manufacturing process. Then, the drug tablet may be filled in. The two halves may then be connected, either by friction fit, glue, or coated over as some examples.

FIG. 11B shows another example of how the sensor pill or tablet 1130 may be fixed into a far end position of the capsule material during the manufacturing process, according to some embodiments. The capsule material may be formed around the sensor 1130 so as to lock in place the sensor at the far end, as shown. A minor amount of crimping 1125 just around the top of the sensor pill or tablet may be sufficient to secure it to the far end of the capsule material. Then, the drug material may be filled in to the rest of the capsule.

In some embodiments, an ingestible sensor may be applied to a plug that is placed on top of the body of a capsule after being filled. The body of the capsule may include the pharmaceutical agent(s), while the plug fastens the body into the capsule compartment, along with the ingestible sensor. The IEM may break free of the plug upon dissolution of the capsule in the stomach fluid, and may thereby activate. In some embodiments, the sensor pill plug can be attached to a capsule cap that has been formed without a dome at the end or had the dome removed after forming. The attachment method between plug and cap can be friction fit, adhesive attachment, or thermal attachment. Such a cap with sensor pill plug would then be able to be processed on standard capsule filling equipment.

In some embodiments, an on-tablet or on-capsule attachment method is defined using a fast release layer between the IEM and the solid oral drug outer surface and a separate mechanical attachment material. The release layer minimizes interactions between the dissolving drug product materials and the IEM, thus ensuring release and IEM activation, and a separate attachment may be used in addition to the release layer for mechanical strength. The mechanical attachment would typically be external to the release layer but does not need to be. Demonstrated examples include the use of a low melting point lipid covering the active IEM areas as a release layer, and an HPC glue attach around the perimeter for mechanical integrity. A perimeter thermal attachment could also be used with the release layer. The release layer may be a soluble material or may be a meltable lipid, and may be dispensed or printed or placed as a film component. Separation of the materials for mechanical attachment and release allows a more broadly tolerant attachment design independent of the surface or dissolution characteristics of the oral drug product. Various dispense, print, or film patterns for both the release layer and the attachment layer may be used to adjust the properties.

In some embodiments, the disclosed methods may include, where practicable, a skirt material that surrounds the ingestible sensor. This material may be configured to expand during activation. The expansion may behave like a jelly fish expanding in water, or like origami that was originally crumpled or compacted and then is made to expand. In other cases, the skirt may inflate via bubbles that are created upon reaction of the ingestible sensor with the conductive fluid. Other methods of expansion include including layers on the skirt that have different rates of thermal expansion, or different interactions with surface tension of water or other conductive fluid.

In some embodiments, the disclosed methods may include pre-fabricated components that can be attached to various capsule pieces during standard manufacturing processes. For example, modified caps or bands may be manufactured to include an ingestible sensor according to any of the described methods herein, and then these pieces may substitute for the standard capsule components and incorporated into the capsule manufacturing process.

Unless specifically stated otherwise, discussions herein using words such as "processing," "computing," "calculating," "determining," "presenting," "displaying," or the like may refer to actions or processes of a computing device 1100 (e.g., a computer) that manipulates or transforms data represented as physical (e.g., electronic, magnetic, or optical) quantities within one or more memories (e.g., volatile memory, non-volatile memory, or any suitable combination thereof), registers, or other computing device components that receive, store, transmit, or display information. Furthermore, unless specifically stated otherwise, the terms "a" or "an" are herein used, as is common in patent documents, to include one or more than one instance. Finally, as used herein, the conjunction "or" refers to a nonexclusive "or," unless specifically stated otherwise.

Although the flowcharts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

The present disclosure is illustrative and not limiting. It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. Further modifications will be apparent to one skilled in the art in light of this disclosure and are intended to fall within the scope of the appended claims.

What is claimed is:

1. A method of manufacturing an ingestible capsule including an ingestible sensor, the method comprising:
   accessing an already-manufactured ingestible capsule; and
   modifying the capsule to include an ingestible sensor using an automated manufacturing process by wedging the ingestible sensor into the capsule and affixing the ingestible sensor to the capsule using friction forces between edges of the ingestible sensor and an inner wall of the ingestible capsule, using the automated manufacturing process,
   wherein the ingestible sensor includes a partial power source that powers the ingestible sensor when the partial power source comes into contact with a conductive fluid.

2. The method of claim 1, wherein the ingestible sensor comprises at least a portion of material that is configured to flex or deform upon applying physical pressure, and wherein wedging the ingestible sensor into the capsule comprises flexing or deforming at least a portion of the ingestible sensor as the ingestible sensor is wedged into the capsule.

3. The method of claim 2, wherein the material that is configured to flex or deform is insoluble and non-conductive and is further configured to magnify a signal emitted from the ingestible sensor by increasing a length of a current path formed between two dissimilar materials positioned on opposite sides of the ingestible sensor.

4. The method of claim 3, wherein the material that is configured to flex and deform comprises a planar geometry.

5. The method of claim 4, wherein the material that is configured to flex and deform comprises a rhombus-shaped planar geometry.

6. The method of claim 4, wherein the material that is configured to flex and deform comprises a planar geometry with at least two lobes.

7. The method of claim 4, wherein the material that is configured to flex and deform comprises a planar geometry with at least two extended arms.

8. A method of manufacturing an ingestible capsule including an ingestible sensor, the method comprising:
   accessing an already-manufactured ingestible capsule; and
   modifying the capsule to include an ingestible sensor using an automated manufacturing process by:
   affixing the ingestible sensor to a first band;
   forming an ingestible sensor band by affixing a second band over the ingestible sensor and the first band to sandwich the ingestible sensor in between the first band and the second band; and
   affixing the ingestible sensor band to the capsule by wrapping the ingestible sensor band around the capsule;
   wherein the ingestible sensor includes a partial power source that powers the ingestible sensor when the partial power source comes into contact with a conductive fluid.

9. The method of claim 8, further comprising affixing the ingestible sensor to the first band using a banding ribbon that is configured to be affixed to multiple ingestible sensors.

10. The method of claim 9, further comprising using a roll-to-roll web-processing manufacturing tool to create the banding ribbon.

11. A method of manufacturing an ingestible capsule including an ingestible sensor, the method comprising:
   accessing an already-manufactured ingestible capsule; and
   modifying the capsule to include an ingestible sensor using an automated manufacturing process by:
   embedding the ingestible sensor onto an inner wall of an outer cap; and
   affixing the outer cap over at least a portion of the capsule, such that the ingestible sensor is sandwiched between at least a portion of the capsule and the outer cap;
   wherein the ingestible sensor includes a partial power source that powers the ingestible sensor when the partial power source comes into contact with a conductive fluid.

12. A method of manufacturing an ingestible capsule including an ingestible sensor, the method comprising:
   accessing an already-manufactured ingestible capsule; and modifying the capsule to include an ingestible sensor using an automated manufacturing process by:
  securing an inner wall of the capsule using a support pin;
  on an outer wall of the capsule, opposite the inner wall of the capsule supported by the support pin, deforming a portion of the outer wall of the capsule to create a depression, using a deforming pin; and
  embedding the ingestible sensor into the depression of the outer wall;
wherein the ingestible sensor includes a partial power source that powers the ingestible sensor when the partial power source comes into contact with a conductive fluid.

13. A method of manufacturing an ingestible capsule including an ingestible sensor, the method comprising:
  accessing an already-manufactured ingestible capsule; and
  modifying the capsule to include an ingestible sensor using an automated manufacturing process by:
    applying a glue material to an inner wall of the capsule; and
    securing the ingestible sensor to the inner wall of the capsule via the glue material;
  wherein the ingestible sensor includes a partial power source that powers the ingestible sensor when the partial power source comes into contact with a conductive fluid.

14. The method of claim 13, wherein the glue material comprises at least one of: polyvinylpyrrolidone (PVP), hydroxypropyl cellulose (HPC), methylcellulose, ethylcellulose, gelatin or hydroxypropyl methylcellulose (HPMC).

15. A method of manufacturing an ingestible capsule including an ingestible sensor, the method comprising:
  accessing an already-manufactured ingestible capsule; and
  modifying the capsule to include an ingestible sensor using an automated manufacturing process by:
    deforming a portion of the capsule by applying heat to the portion of the capsule; and
    attaching the ingestible sensor to the deformed portion of the capsule;
  wherein the ingestible sensor includes a partial power source that powers the ingestible sensor when the partial power source comes into contact with a conductive fluid.

16. A method of manufacturing an ingestible capsule including an ingestible sensor, the method comprising:
  accessing an already-manufactured ingestible capsule; and
  modifying the capsule to include an ingestible sensor using an automated manufacturing process by attaching an ingestible sensor bead to the capsule using a fluid bed coating;
  wherein the ingestible sensor includes a partial power source that powers the ingestible sensor when the partial power source comes into contact with a conductive fluid.

17. A method of manufacturing an ingestible capsule including an ingestible sensor, the method comprising:
  accessing an already-manufactured ingestible capsule; and
  modifying the capsule to include an ingestible sensor using an automated manufacturing process by machining a vertical channel into a rounded end of the capsule and placing the ingestible sensor into the vertical channel;
  wherein the ingestible sensor includes a partial power source that powers the ingestible sensor when the partial power source comes into contact with a conductive fluid.

18. The method of claim 17, wherein machining the vertical channel comprises machining a bottom edge into the capsule having a geometry that matches a geometry of an outer edge of the ingestible sensor.

19. The method of claim 18, wherein the bottom edge of the vertical channel comprises a V-shaped edge.

* * * * *